United States Patent
Sun et al.

(10) Patent No.: US 10,268,114 B2
(45) Date of Patent: Apr. 23, 2019

(54) HIGH PERFORMANCE QUARTZ CRYSTAL MICROBALANCE ENHANCED BY MICROSTRUCTURES FOR BIOLOGICAL APPLICATIONS

(71) Applicant: UNIVERSITY OF MASSACHUSETTS, Boston, MA (US)

(72) Inventors: Hongwei Sun, Lexington, MA (US); Pengtao Wang, Lowell, MA (US); Junwei Su, Lowell, MA (US)

(73) Assignee: University of Massachusetts, Boston, MA (US)

( * ) Notice: Subject to any disclaimer, the term of this patent is extended or adjusted under 35 U.S.C. 154(b) by 537 days.

(21) Appl. No.: 14/936,566

(22) Filed: Nov. 9, 2015

(65) Prior Publication Data

US 2016/0131615 A1    May 12, 2016

Related U.S. Application Data

(60) Provisional application No. 62/076,755, filed on Nov. 7, 2014, provisional application No. 62/251,624, filed on Nov. 5, 2015.

(51) Int. Cl.
| | |
|---|---|
| *G03F 7/00* | (2006.01) |
| *G01N 29/02* | (2006.01) |
| *G01N 29/44* | (2006.01) |
| *G03F 7/038* | (2006.01) |
| *G01N 29/036* | (2006.01) |

(52) U.S. Cl.
CPC ......... *G03F 7/0002* (2013.01); *G01N 29/022* (2013.01); *G01N 29/036* (2013.01); *G01N 29/4418* (2013.01); *G01N 29/4472* (2013.01); *G03F 7/038* (2013.01); *G01N 2291/014* (2013.01); *G01N 2291/0257* (2013.01); *G01N 2291/0426* (2013.01)

(58) Field of Classification Search
CPC ..... G03F 7/0002; G03F 7/038; G01N 29/022; G01N 29/036; G01N 29/4418; G01N 29/4472
See application file for complete search history.

(56) References Cited

PUBLICATIONS

Zhang, Kai, et al. "A microfluidic system with surface modified piezoelectric sensor for trapping and detection of cancer cells." Biosensors and Bioelectronics 26.2 (2010): 935-939.*

Kamei, Daisuke, Hiroharu Ajiro, and Mitsuru Akashi. "Morphological changes of isotactic poly (methyl methacrylate) thin films via self-organization and stereocomplex formation." Polymer journal 42.2 (2010): 131.*

Wang, Pengtao, et al. "Ultrasensitive quartz crystal microbalance enabled by micropillar structure." Applied Physics Letters 104.4 (2014): 043504.*

Wang, Pengtao, et al. "An ultrasensitive quartz crystal microbalance-micropillars based sensor for humidity detection." Journal of Applied Physics 115.22 (2014): 224501.*

* cited by examiner

*Primary Examiner* — Robert J Eom
(74) *Attorney, Agent, or Firm* — Milstein Zhang & Wu LLC

(57) ABSTRACT

Quartz crystal microbalance resonators are described, as are methods of making them using micron sized pillar array of polymethyl methacrylate fabricated on a QCM surface using a nanoimprint lithography process. Their use in any applications, including for example gas and liquid sensors and biosensors as well as other measurement applications, is also discussed.

13 Claims, 39 Drawing Sheets

Micro-26 R
Height of Pillar= 5μm

REF (MicroChem)
Height of Pillar= 10μm

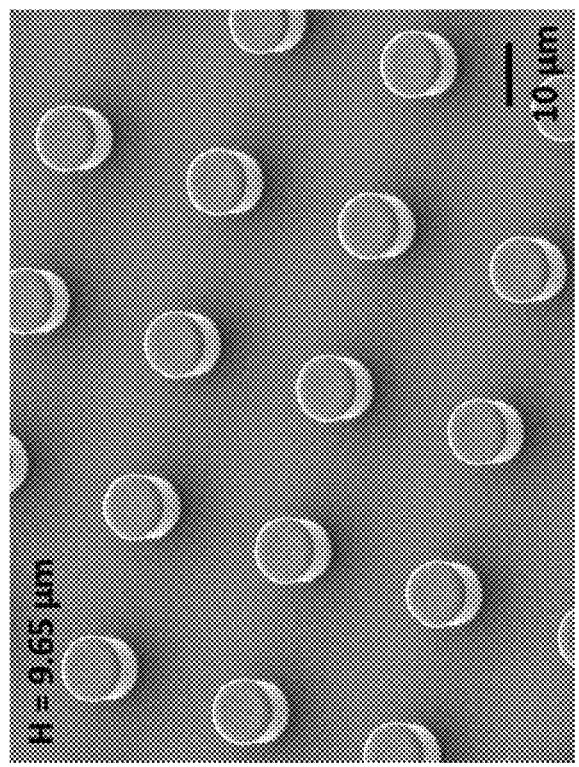
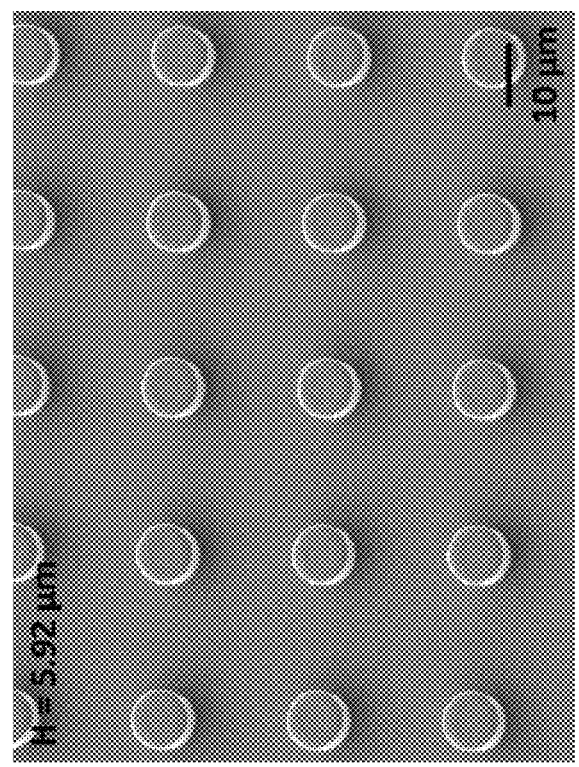
FIG. 3B
FIG. 3A

FIG. 4C
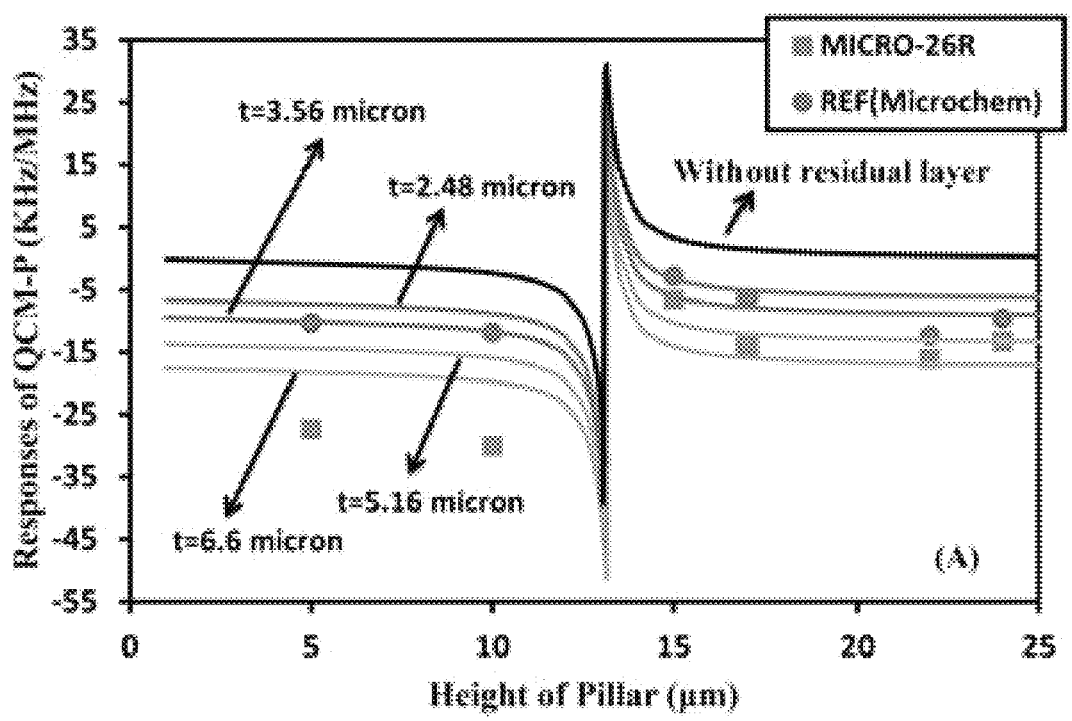
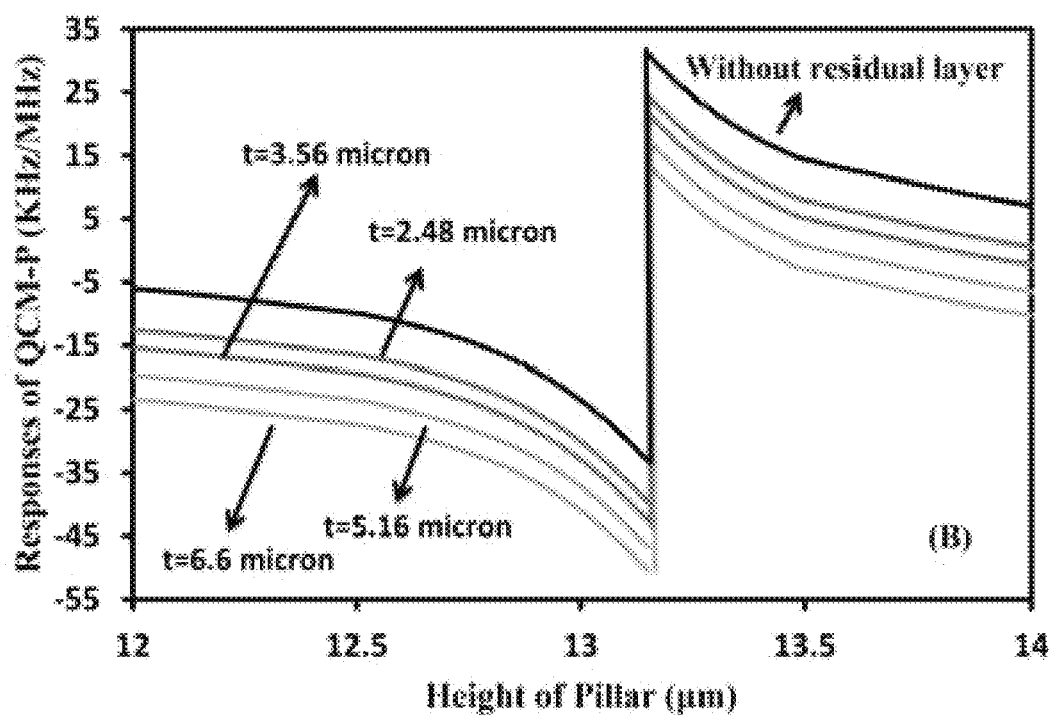
FIG. 4D

Two important observations concerning the beam modes:

1. Note the existence of certain nodal points with zero displacement at all times; the higher the mode the greater the number of these nodal points 2. Also note the substantial differences in the frequency (speed) of the vibration for different modes!

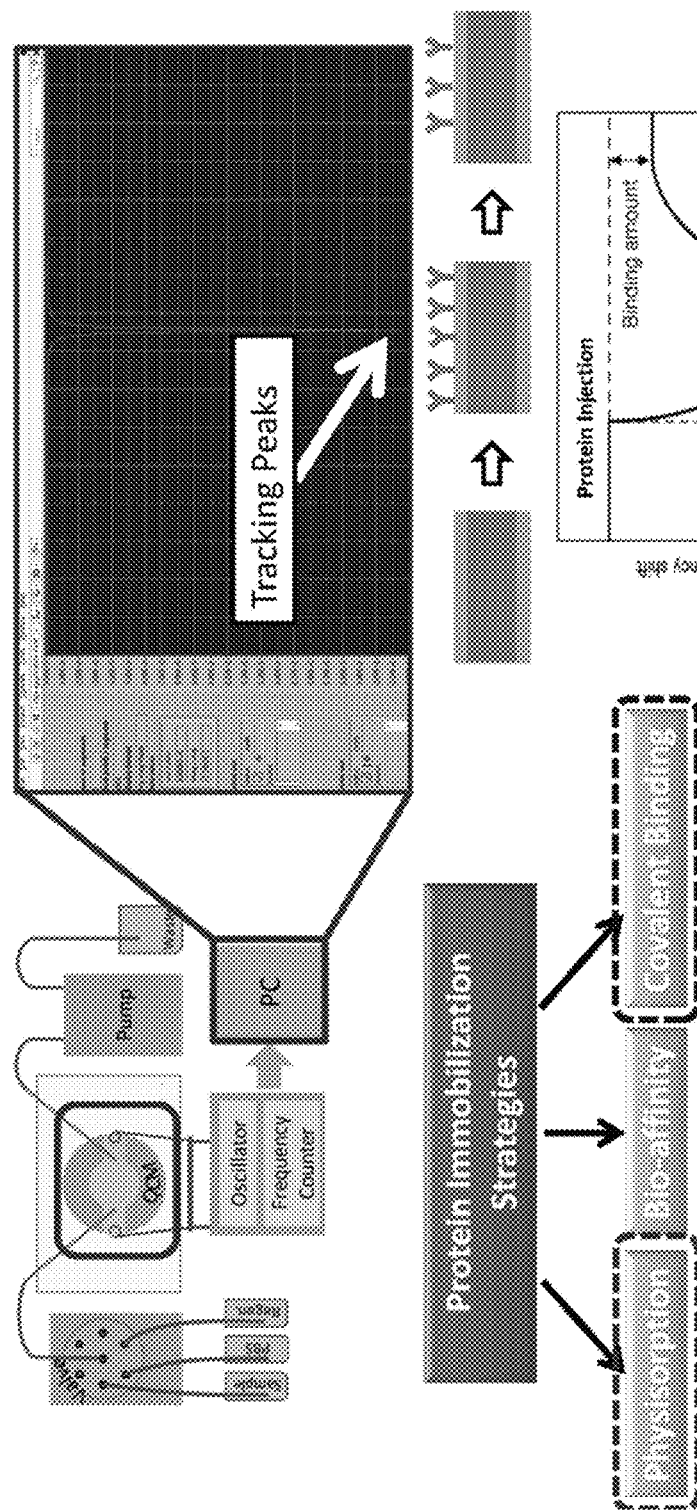

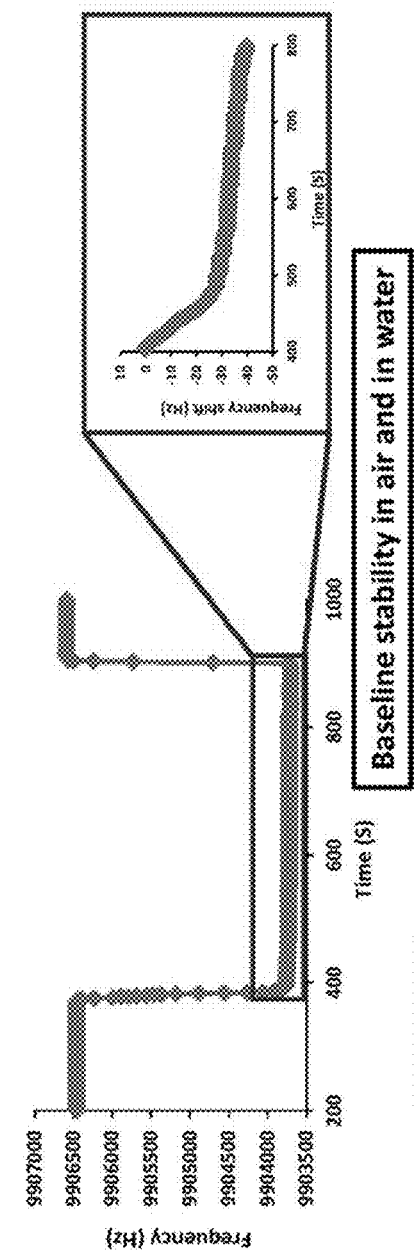
FIG. 30A
FIG. 30B
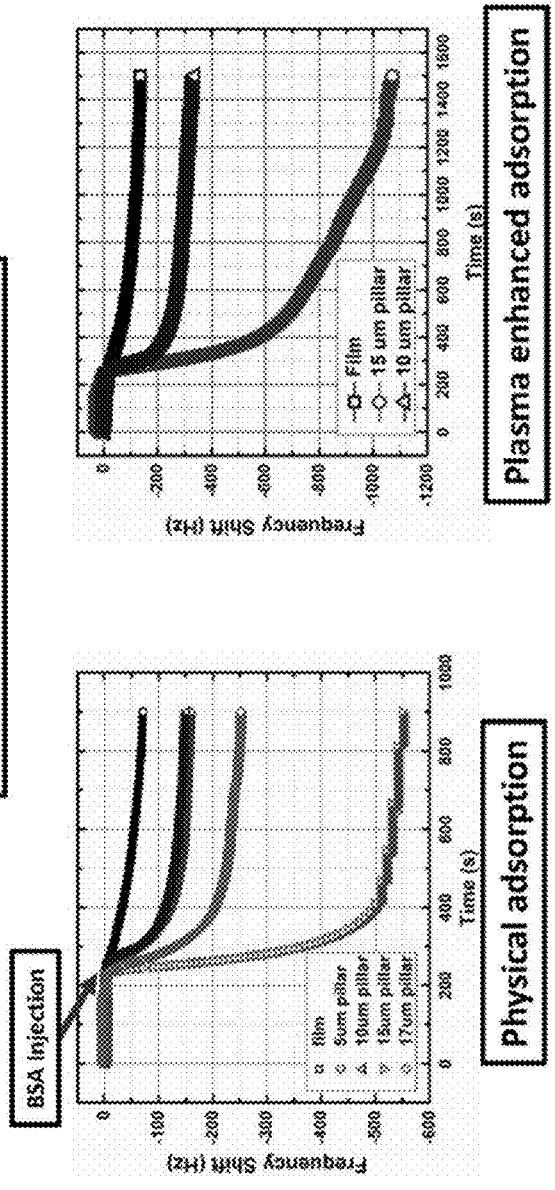
FIG. 30C
FIG. 30D

BSA conc.=0.015 mM
Molar ratio of BSA: fluoresce probe(tetramethylrhodamine-5-maleimide)= 1: 11
PBS: 20mM sodium phosphate, pH 7.2, 150mM sodium phosphate Sample treatment after plasma:

1#: 1000 μL PBS

2#: 50 μL EDC+ 50 μL NHS mixed freshly +900 μL labeled BSA

3#: 5 μL EDC+ 5 μL NHS mixed freshly +90 μL water
→ React with PMMA for 10 min
→ Rinse with water
→ React with 900 μL labeled BSA+100 μL PBS 2.5 h of incubation shaken at low rpm Wash off unbonded BSA with PBS

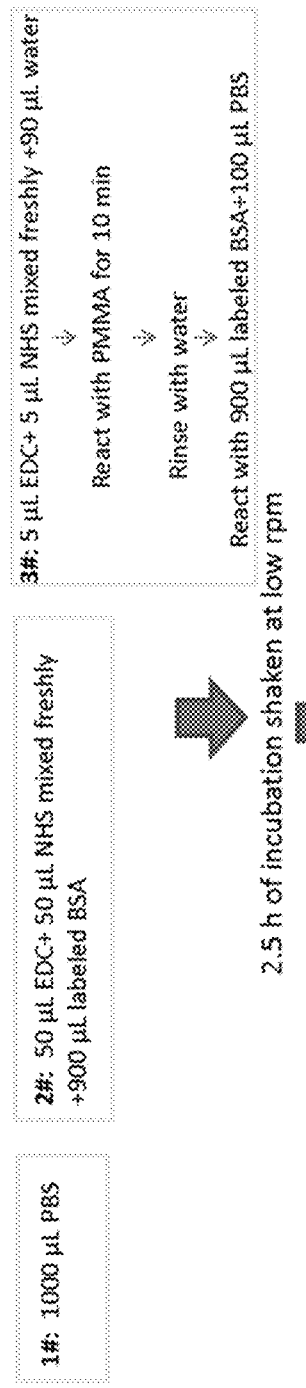

FIG. 32A

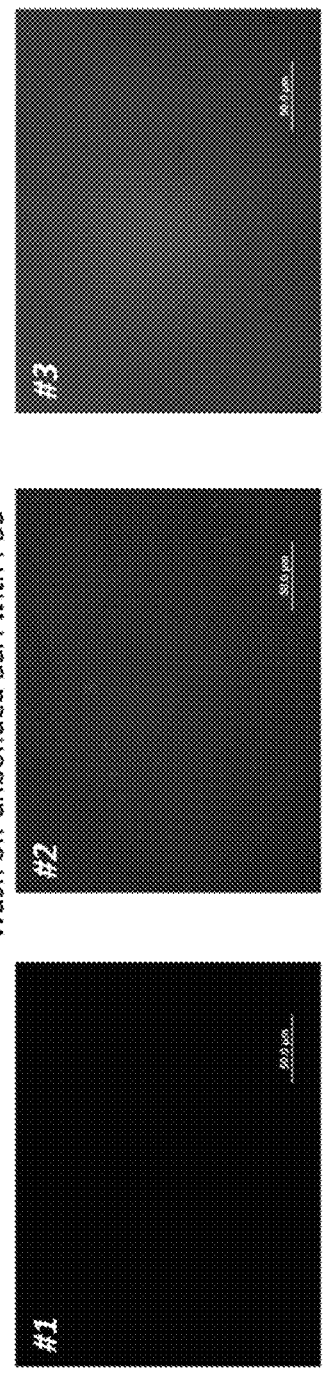

HIGH PERFORMANCE QUARTZ CRYSTAL MICROBALANCE ENHANCED BY MICROSTRUCTURES FOR BIOLOGICAL APPLICATIONS

CROSS-REFERENCE TO RELATED APPLICATIONS

This application claims priority to and the benefit of U.S. provisional patent application Ser. No. 62/076,755, filed Nov. 7, 2014, and U.S. provisional patent application Ser. No. 62/251,624, filed Nov. 5, 2015, each of which applications is incorporated herein by reference in its entirety.

STATEMENT REGARDING FEDERALLY FUNDED RESEARCH OR DEVELOPMENT

This invention was made with government support under contracts ECCS 0731125 AND CMMI 0923403 awarded by the National Science Foundation (NSF). The government has certain rights in the invention.

FIELD OF THE INVENTION

The invention relates to microbalances in general and particularly to quartz crystal microbalances.

BACKGROUND OF THE INVENTION

Quartz crystal microbalances (QCM) have been extensively used in sensing the mass loading with extremely high sensitivity ($<10$ ng/cm$^2$). A QCM device typically consists of a thin disk of AT-cut quartz crystal with circular electrodes patterned on both sides. Due to the piezoelectric properties and crystalline orientation of the quartz, the alternating voltage between the electrodes results in a shear waves within the crystal. For this reason, QCM is sometimes referred to as a thickness shear mode resonator (TSM)) in the literature. With a film with certain mass attached on one side of the electrode, the resonant properties such as resonant frequency and bandwidth of the QCM will be changed accordingly.

The relationship between the resonant frequency shift, $\Delta f$, and surface mass density, $\Delta m/A$ of a thin and rigid film on QCM, can be expressed as Sauerbrey theory $$\Delta f = \frac{1}{C}\frac{\Delta m}{A} \quad (1)$$

where C is the mass sensitivity coefficient which is given by $$C = \frac{\sqrt{\mu_q \rho_q}}{2f^2} \quad (2)$$

where $\rho_q$ is the density of quartz crystal, $\mu_q$ is the shear modulus of quartz crystal, and $f_0$ is resonant frequency of the QCM without mass loading.

Substituting Eqn. (2) into Eqn. (1), one obtains Eqn. 3):

$$\Delta f = -\frac{2f_0^2}{\sqrt{\mu_q \rho_q}}\frac{\Delta m}{A} \quad (3)$$

The mass loading on the QCM normally results in a negative resonant frequency shift, as illustrated by the negative sign.

For a typical 10 MHz QCM, the value of C is 4.42 ng/cm$^2$/Hz. As indicated by Eqn. (2), a higher resonant frequency is needed to achieve better sensitivity of QCM. Unfortunately, a higher resonant frequency requires a thinner quartz crystal, which makes the crystal become extremely fragile and the high resonant frequency also leads to higher energy dissipation when the QCM operate in a liquid environment.

In applications such as QCM based biosensors, one side electrode is usually functionalized by coating a thin film of polymer to attach biomolecules. However, the sensitivity of the QCM is compromised since the signal of the QCM could be significantly damped down due to the viscoelastic response of the polymer to the acoustic wave transmission. The situation may get much worse with the increasing of the film thickness. Intensive research effort has been concentrated on utilizing micro- and nano-scale structures to increase the sensing area of QCM in order to improve the response of QCM. Special fabrication techniques are required for these micro/nanostructures, which furthermore result in sophisticate structure-acoustic wave interactions. This makes the signal analysis very challenging.

Sauerbrey theory (as expressed by Eqn. (1)), indicates negative resonant frequency shift resulted from the mass loading on QCM. However, Dybward first reported an increased resonant frequency with gold spheres (10-50 μm in diameter) placed on the surface of a QCM device, and the increase of resonant frequency was dependent of the bonding force between particles and substrate. Pomorska et al. observed the positive resonant frequency shift when large diameter colloidal objects (>1 μm) were absorbed on QCM surface in liquid. Olofsson et al. used QCM to investigate the bacterial growth on the surface of stainless steel and found that the exponentially grown cells gave rise to a positive resonant frequency shift as long as their cell surface was hydrophilic. Dultsev and Kolosovsky mathematically demonstrated a positive resonant frequency shift caused by a single biological nano-sized particle. Castro et al. found a punctual rigid load applied on the QCM played as an apparent negative mass or resulting in positive frequency shift through both experiments and numerical simulation. Zhang et al. studied the deviations of frequency shift from Sauerbrey equation caused by finite size circular particles, and a frequency-dependent effective particle mass was introduced to classify and characterize different aspects of the particle-induced frequency shifts. Ramkrishnan et al. reported the positive frequency response when high aspect ratio structures were fabricated over surface acoustic wave (SAW) sensors, Olsson et al. classified the particle loading on QCM as "inertial loading" and "elastic loading". The inertial loading resulted in a negative resonant frequency shift as described by Sauerbrey's theory while the "elastic loading" yielded a positive resonant frequency shift due to the coupled vibration. A coupled-resonance model was developed to quantitatively investigate the positive resonant frequency shift with elastic loading of particles. In this two-degree of freedom system, the QCM was treated as the main resonator with resonant of $f_0$, and the particle attached on QCM surface played as a second resonator with its RF, $f_s$. When a micro size particle was loaded on QCM, the contact area was limited to a small value and cause "elastic loading". Furthermore, the resonant frequency of the particle attached to QCM is much smaller than that of original QCM, which results in a reduced resonant frequency of the coupled system. In this case, the positive resonant frequency shift become possible, which was proportional to the stiffness/elasticity of contact rather than the mass of particles.

There is a need for systems and methods that provide improved sensitivity.

REFERENCES

1. C. Lu and O. Lewis. J. Appl. Phys. 43(11), 4385-4390 (1972).
2. E. Benes. J. Appl. Phys. 56(3), 608-626 (1984).
3. V. E. Granstaff and S. J. Martin. J. Appl. Phys. 75(3), 1319-1329 (1994).
4. R. D. Williams, A. K. Upadhyayula and V. R. Bhethanabotla. Sens. Actuators.
B. 122(2), 635-643 (2007).
5. G. Sauerbery, Z. Phys. 155(2), 206-222 (1959).
6. F. Liu, X. Liu, S. Ng, and H. S. Chan, Sens. Actuators. B. 113(1), 234-240 (2006).
7. C. Lee, T. Yan, and T. Wang, Sens. Actuators. B. 166-167, 165-171 (2012).
8. D. A. Brass and K. R. Shull, J. Appl. Phys. 103(7), 073517 (2008).
9. C. R. Evans, G. McHale, N. J. Shirtcliffe, S. M. Stanley and M. I. Newton,
Sens. Actuators. A 123-124, 73-76 (2005).
10. P. Roach, G. McHale, C. R. Evans, N. J. Shirtcliffe and M. I. Newton,
Langmuir 23(19), 9823-9830 (2007).
11. G. L. Dybwad, J. Appl. Phys. 58(7), 2789 (1985).
12. A. Pomorska, D. Shchukin, R. Hammond, M. Cooper, G. Grundmeier and D.
Johannsmann, Anal. Chem. 82(6), 2237-2242 (2010).
13. A. C. Olofsson, M. Hermansson, and H. Elwing, Appl. Environ. Microbiol.
71(5), 2705-2712 (2005).
14. F. N. Dultsev, and E. A. Kolosovsky, Sens. Actuators. B. 143(1), 17-24 (2009).
15. P. Castro, P. Resa, and L. Elvira, I O P Conf. Ser.: Mater. Sci. Eng. 42, 012046 (2012).
16. C. Zhang, N. Liu, J. Yang, and W. Chen, IEEE Trans Ultrason Ferroelectr Freq Control 58(3), 666-670 (2011).
17. N. Ramkrishnan, R. P. Palathinkal, and H. B. Nemade, Sensor Lett. 8(2), 253-257 (2010).
18. N. Ramkrishman, H. B. Nemade and R. P. Palathinkal, IEEE Sens. J. 11(2),
430-431 (2011).
19. N. Ramkrishman, H. B. Nemade and R. P. Palathinkal, Sensors 12(4), 3789-3797 (2012).
20. A. L. Olsson, H. C. van de Mei, D. Johannsmann, H. J. Busscher, and P. K.
Sharma, Anal. Chem. 84(10), 4504-4512 (2012).
21. J. Xie, H. Wang, Y. Lin, Y. Zhou, and Y. Wu, Sens. Actuator. B 177, 1083 (2013).
22. Y. Zhang, K. Yu, S. Ouyang, L. Luo, H. Hu, Q. Zhang, and Z. Zhu, Physica B 368, 94 (2005).
23. W. Hu, S. Chen, B. Zhou, L. Liu, B. Ding, and H. Wang, Sens. Actuator. B 159, 301 (2011).
24. H. Y. Yoo, and S. Bruckenstein, Anal. Chim. Acta. 785, 98 (2013).
25. Beér J M. High efficiency electric power generation: The environmental role. *Progress in Energy and Combustion Science* 33, 107-134 (2007).
26. Khawaji A D, Kutubkhantableah I K, Wie J-M. Advances in seawater desalination technologies. *Desalination* 221, 47-69 (2008).
27. Humplik T, et al. Nanostructured materials for water desalination. *Nanotechnology* 22, 292001 (2011).
28. Lee A, Moon M-W, Lim H, Kim W-D, Kim H-Y. Water harvest via dewing. *Langmuir* 28, 10183-10191 (2012).
29. Beysens D. Dew nucleation and growth. *Comptes Rendus Physique* 7, 1082-1100 (2006).
30. Boreyko J B, Chen C-H. Vapor chambers with jumping-drop liquid return from superhydrophobic condensers. *International Journal of Heat and Mass Transfer* 61, 409-418 (2013).
31. Dietz C, Rykaczewski K, Fedorov A G, Joshi Y. Visualization of droplet departure on a superhydrophobic surface and implications to heat transfer enhancement during dropwise condensation. *Applied Physics Letters* 97, 033104 (2010).
32. Park K-C, Choi H J, Chang C-H, Cohen R E, McKinley G H, Barbastathis G. Nanotextured Silica Surfaces with Robust Superhydrophobicity and Omnidirectional Broadband Supertransmissivity. *ACS Nano* 6, 3789-3799 (2012).
33. Schmidt E, Schurig W, Sellschopp W. Versuche über die Kondensation von Wasserdampf in Film- und Tropfenform. *Technische Mechanik und Thermodynamik* 1, 53-63 (1930).
34. Lau K K S, et al. Superhydrophobic Carbon Nanotube Forests. *Nano Letters* 3, 1701-1705 (2003).
35. Bisetto A, Torresin D, Tiwari M K, Col D D, Poulikakos D. Dropwise condensation on superhydrophobic nanostructured surfaces: literature review and experimental analysis. *Journal of Physics: Conference Series* 501, 012028 (2014).
36. Yong Chae J, Bharat B. Contact angle, adhesion and friction properties of micro- and nanopatterned polymers for superhydrophobicity. *Nanotechnology* 17, 4970 (2006).
37. Takahiro I, Nagahiro S, Yasushi I, Makoto B, Osamu T. Fabrication and characterization of ultra-water-repellent alumina-silica composite films. *Journal of Physics D: Applied Physics* 40, 192 (2007).
38. Öner D, McCarthy T J. Ultrahydrophobic Surfaces. Effects of Topography Length Scales on Wettability. *Langmuir* 16, 7777-7782 (2000).
39. He M, Li H, Wang J, Song Y. Superhydrophobic surface at low surface temperature. *Applied Physics Letters* 98, 093118 (2011).
40. Burton Z, Bhushan B. Hydrophobicity, Adhesion, and Friction Properties of Nanopatterned Polymers and Scale Dependence for Micro- and Nanoelectromechanical Systems. *Nano Letters* 5, 1607-1613 (2005).
41. Feng L, et al. Creation of a Superhydrophobic Surface from an Amphiphilic Polymer. *Angewandte Chemie International Edition* 42, 800-802 (2003).
42. Ma M, Hill R M, Lowery J L, Fridrikh S V, Rutledge G C. Electrospun Poly(Styrene-block-dimethylsiloxane) Block Copolymer Fibers Exhibiting Superhydrophobicity. *Langmuir* 21, 5549-5554 (2005).
43. Wong T-S, et al. Bioinspired self-repairing slippery surfaces with pressure-stable omniphobicity. *Nature* 477, 443-447 (2011).
44. Buck M E, Schwartz S C, Lynn D M. Superhydrophobic Thin Films Fabricated by Reactive Layer-by-Layer Assembly of Azlactone-Functionalized Polymers. *Chemistry of Materials* 22, 6319-6327 (2010).
45. Miljkovic N, Enright R, Wang E N. Effect of Droplet Morphology on Growth Dynamics and Heat Transfer during Condensation on Superhydrophobic Nanostructured Surfaces. *ACS Nano* 6, 1776-1785 (2012).

46. Dorrer C, Rühe J. Condensation and Wetting Transitions on Microstructured Ultrahydrophobic Surfaces. *Langmuir* 23, 3820-3824 (2007).
47. Narhe R D, Beysens D A. Nucleation and Growth on a Superhydrophobic Grooved Surface. *Physical Review Letters* 93, 076103 (2004).
48. Narhe R D, Beysens D A. Growth Dynamics of Water Drops on a Square-Pattern Rough Hydrophobic Surface. *Langmuir* 23, 6486-6489 (2007).
49. Boreyko J B, Chen C-H. Self-Propelled Dropwise Condensate on Superhydrophobic Surfaces. *Physical Review Letters* 103, 184501 (2009).
50. Rykaczewski K. Microdroplet Growth Mechanism during Water Condensation on Superhydrophobic Surfaces. *Langmuir* 28, 7720-7729 (2012).
51. Rykaczewski K, Scott J H J, Rajauria S, Chinn J, Chinn A M, Jones W.
Three dimensional aspects of droplet coalescence during dropwise condensation on superhydrophobic surfaces. *Soft Matter* 7, 8749-8752 (2011).
52. Enright R, Miljkovic N, Al-Obeidi A, Thompson C V, Wang E N. Condensation on Superhydrophobic Surfaces: The Role of Local Energy Barriers and Structure Length Scale. *Langmuir* 28, 14424-14432 (2012).
53. Liu T, Sun W, Li X, Sun X, Ai H. Growth modes of condensates on nano-textured surfaces and mechanism of partially wetted droplet formation. *Soft Matter* 9, 9807-9815 (2013).
54. Rykaczewski K, et al. How nanorough is rough enough to make a surface superhydrophobic during water condensation? *Soft Matter* 8, 8786-8794 (2012).
55. Feng J, Pang Y, Qin Z, Ma R, Yao S. Why Condensate Drops Can Spontaneously Move Away on Some Superhydrophobic Surfaces but Not on Others. *ACS Applied Materials & Interfaces* 4, 6618-6625 (2012).
56. Miljkovic N, et al. Jumping-Droplet-Enhanced Condensation on Scalable Superhydrophobic Nanostructured Surfaces. *Nano Letters* 13, 179-187 (2013).
57. Paxson A T, Yagüe J L, Gleason K K, Varanasi K K. Stable Dropwise Condensation for Enhancing Heat Transfer via the Initiated Chemical Vapor Deposition (iCVD) of Grafted Polymer Films. *Advanced Materials* 26, 418-423 (2014).
58. Zhang G, Wu C. Quartz Crystal Microbalance Studies on Conformational Change of Polymer Chains at Interface. *Macromolecular Rapid Communications* 30, 328-335 (2009).
59. Baranova N S, et al. The Inflammation-associated Protein TSG-6 Cross-links Hyaluronan via Hyaluronan-induced TSG-6 Oligomers. *Journal of Biological Chemistry* 286, 25675-25686 (2011).
60. Zan X, Peng B, Hoagland D A, Su Z. Polyelectrolyte uptake by PEMs: Impact of salt concentration. *Polymer Chemistry* 2, 2581-2589 (2011).
61. Gomes M T S R, Rocha T A, Duarte A C, Oliveira J A B P. Performance of a tetramethylammonium fluoride tetrahydrate coated piezoelectric crystal for carbon dioxide detection. *Analytica Chimica Acta* 335, 235-238 (1996).
62. Ding B, Kim J, Miyazaki Y, Shiratori S. Electrospun nanofibrous membranes coated quartz crystal microbalance as gas sensor for NH3 detection. *Sensors and Actuators B: Chemical* 101, 373-380 (2004).
63. Nomura T, Okuhara M. Frequency shifts of piezoelectric quartz crystals immersed in organic liquids. *Analytica Chimica Acta* 142, 281-284 (1982).
64. Auge J, Hauptmann P, Eichelbaum F, Rosier S. Quartz crystal microbalance sensor in liquids. *Sensors and Actuators B: Chemical* 19, 518-522 (1994).
65. Yang M, Thompson M. Multiple chemical information from the thickness shear mode acoustic wave sensor in the liquid phase. *Analytical Chemistry* 65, 1158-1168 (1993).
66. Onda T, Shibuichi S, Satoh N, Tsujii K. Super-Water-Repellent Fractal Surfaces. *Langmuir* 12, 2125-2127 (1996).
67. Wang P, Su J, Su C-F, Dai W, Cernigliaro G, Sun H. An ultrasensitive quartz crystal microbalance-micropillars based sensor for humidity detection. *Journal of Applied Physics* 115, 224501 (2014).
68. Im J, Chandekar A, Whitten J E. Anomalous Vapor Sensor Response of a Fluorinated Alkylthiol-Protected Gold Nanoparticle Film. *Langmuir* 25, 4288-4292 (2009).
69. Chen X, et al. Nanograssed Micropyramidal Architectures for Continuous Dropwise Condensation. *Advanced Functional Materials* 21, 4617-4623 (2011).
70. Sikarwar B S, Khandekar S, Agrawal S, Kumar S, Muralidhar K. Dropwise Condensation Studies on Multiple Scales. *Heat Transfer Engineering* 33, 301-341 (2011).

SUMMARY OF THE INVENTION

According to one aspect, the invention features a quartz crystal microbalance resonator, comprising: a quartz oscillator having a surface and having electrical input terminals, and a plurality of micropillars of a resonant material in an array, each of the micropillars having a chemical composition, a diameter, a length, and a spacing, the plurality of micropillars in mechanical communication with the surface of the quartz oscillator, the quartz microbalance resonator having at least one characteristic resonant frequency.

In one embodiment, a residual layer is situated between the plurality of micropillars and the quartz oscillator.

In another embodiment, the at least one characteristic resonant frequency has a dependence on the diameter.

In yet another embodiment, the at least one characteristic resonant frequency has a dependence on the length.

In still another embodiment, the at least one characteristic resonant frequency has a dependence on the spacing.

In a further embodiment, the quartz crystal microbalance resonator is configured to operate in contact with a fluid medium.

In a further embodiment, the fluid medium is a gas.

In a further embodiment, the fluid medium is a liquid.

In yet a further embodiment, the resonant material is polymethyl methacrylate.

In an additional embodiment, the resonant material is a polymer.

In one more embodiment, the quartz crystal microbalance resonator is configured to modify the at least one characteristic resonant frequency in response to a quantity of adsorbed material on the plurality of micropillars.

According to another aspect, the invention relates to a method of fabricating a quartz crystal microbalance resonator, comprising the steps of: providing a quartz oscillator having a surface and having electrical input terminals; providing a nanoimprint lithography mother mold; providing a transfer mold using the nanoimprint lithography mother mold as a template; using the transfer mold to prepare an array of micropillars made from a resonant material; and attaching the array of micropillars to the surface of the quartz oscillator, thereby fabricating the quartz crystal microbalance resonator.

In one embodiment, the nanoimprint lithography mother mold comprises SU-8 resin

In another embodiment, the transfer mold comprises PDMS.

In yet another embodiment, the resonant material is polymethyl methacrylate.

According to another aspect, the invention relates to a method of operating a quartz crystal microbalance resonator, comprising the steps of: providing a quartz crystal microbalance resonator, comprising: a quartz oscillator having a surface and having electrical input terminals, and a plurality of pillars of a resonant material in an array, each of the pillars having a chemical composition, a diameter, a length, and a spacing, the plurality of pillars in mechanical communication with the surface of the quartz oscillator; the quartz microbalance resonator having at least one characteristic resonant frequency; operating the quartz crystal microbalance resonator to determine one of the at least one characteristic resonant frequency; adsorbing a quantity of a substance on the plurality of pillars; operating the quartz crystal microbalance resonator to determine a frequency shift in the one of the at least one characteristic resonant frequency; calculating a value of a mass of the quantity of the substance that was adsorbed on the plurality of pillars from the frequency shift; and performing at least one of recording the value, transmitting the value to a data handling system, or to displaying the value to a user.

In one embodiment, the at least one characteristic resonant frequency is a fundamental frequency.

In another embodiment, the at least one characteristic resonant frequency is a first harmonic frequency.

In yet another embodiment, the at least one characteristic resonant frequency is a second harmonic frequency.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 3A through FIG. 3F are images of microstructure patterned PMMA surface with various heights.

FIG. 4C is a graph showing the response of QCM-P devices versus heights of micro-pillars and comparison with theoretical model with considering the effect of a residual layer.

FIG. 4D is a graph showing the response of QCM-P devices versus heights of micro-pillars and comparison with theoretical model with considering the effect of a residual layer.

In FIG. 12A thorough FIG. 12C the inset is the contact angle image for each case.

FIG. 29A is schematic diagram for an apparatus used to measure biological binding activity with QCM-P devices embodying principles of the invention.

FIG. 29B is a close-up of a screen shot showing data obtained in a measurement of biological binding activity with QCM-P devices embodying principles of the invention.

FIG. 29C is a schematic graph showing the time evolution of a measurement signal of biological binding activity with QCM-P devices embodying principles of the invention.

FIG. 30A is a graph of frequency vs. time for a measurement of biological binding activity with QCM-P devices embodying principles of the invention.

FIG. 30B is a close-up of the data in FIG. 30A.

FIG. 30C is a graph of frequency vs. time for a measurement of biological binding activity based on physical adsorption with a variety of QCM-P devices embodying principles of the invention.

FIG. 30D is a graph of frequency vs. time for a measurement of biological binding activity based on plasma enhanced adsorption with a variety of QCM-P devices embodying principles of the invention.

FIG. 32A is an image of a reference fluorescence slide.

FIG. 32B is an image of a fluorescence slide with BSA.

FIG. 32C is an image of a fluorescence slide with BSA and PBS.

DETAILED DESCRIPTION

The invention relates to quartz crystal microbalances (QCM) fabricated using micron sized pillar array of polymethyl methacrylate (PMMA) fabricated on a QCM surface using a nanoimprint lithography (NIL) process. Operation of such microbalances is demonstrated.

While the document titled "Ultrasensitive quartz crystal microbalance enabled by micropillar structure" was published on Jan. 30, 2014, it is believed that the rights of the inventors to file for and receive a valid U.S. Patent are not precluded thereby.

NOMENCLATURE

A Surface area
E Young's modulus
$f_0$ Resonant frequency of bare QCM
$f_p$ Resonant frequency of micro-pillar
G Shear modulus of residual layer
H Height of the micro-pillar
$h_s$ Thickness of quartz
I Moment of inertia
$K_p$ Force constant of micro-pillar
$K_q$ Force constant of QCM
$M_n$ Number average molecular weight
$M_p$ Mass of micro-pillar
$M_q$ Mass of QCM
$M_w$ Weight average molecular weight
Pd Polydispersity
PDMS Polydimethyl siloxane
PMMA Polymethyl methacrylate
QCM Quartz Crystal Microbalance
SEM Scanning Electron Microscope
t Residual layer thickness
T-NIL Thermal nano-imprinting lithography

GREEK SYMBOLS

φ Acoustic phase shift
ω Frequency
$\rho_q$ Density of quartz
$\mu_q$ Shear stiffness of quartz
$\rho_s$ Surface mass density of residual layer Fabrication of QCM-P Nanoimprinting is a state-of-the-art lithography/patterning technology for fabricating nanostructures on polymeric materials with low-cost, high-throughput and high-resolution. The NIL generates nanopatterns using a mechanical embossing principle that effectively overcomes the limitations set by light diffractions or beam scattering of conventional lithography tools. The sub-10 nm features have been successfully imprinted. The NIL uses a hard mold that contains nanoscale features defined on its surface to emboss into polymer material casted on the wafer substrate under controlled temperature and pressure conditions. The curing by heating or UV light during imprinting will solidify the polymer nanostructures with mechanical integrity.

PMMA micro-pillars with different heights (5 μm-24 μm) were fabricated on the QCM substrates (MicroChem Corp., Newton, Mass.). The thickness of the residual layer generated during T-NIL is controlled by varying the spin coating speed and imprinting pressure. For the QCM-P device, this residual layer enhances the adhesion of micro-pillars to the QCM surface. But the thick residual layer will result in a large signal damping and reducing the response of QCM-P. The measurement of the residual layer is performed using both Dektak and the Scanning Electron Microscope (SEM) (Core Research Facilities, UML).

Figure 1:
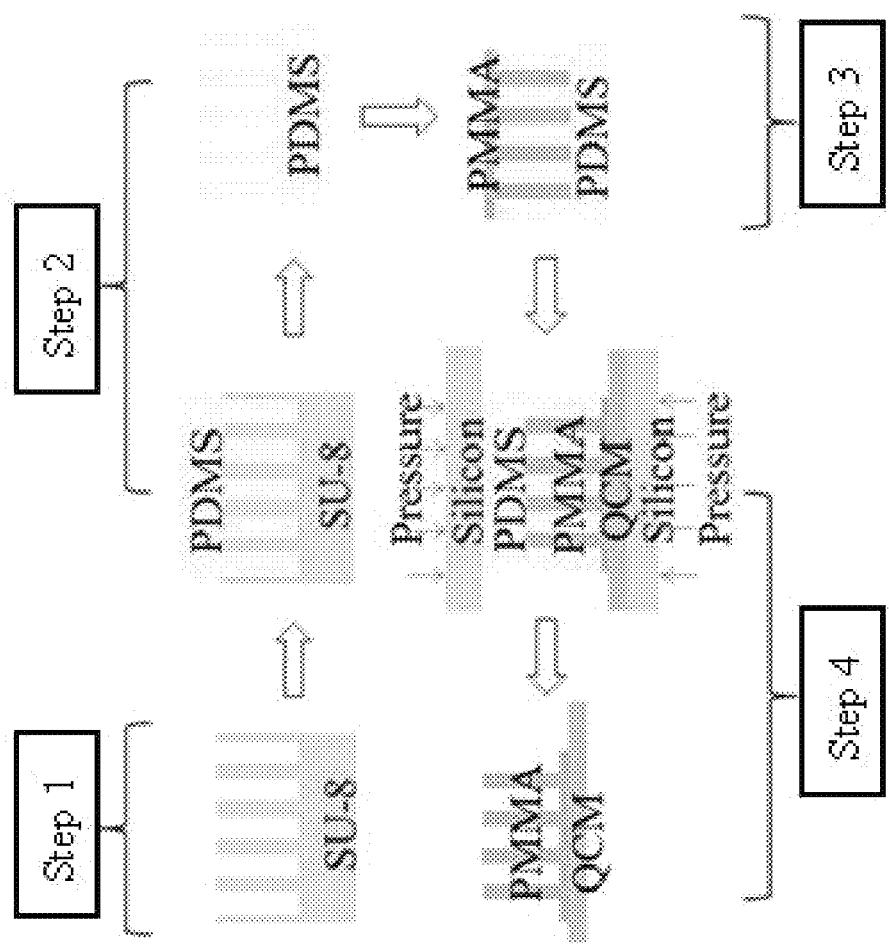
FIG. 1 is a schematic illustration of the nanoimprinting procedure, including four steps for fabricating QCM-P devices with T-NIL.

Nanoimprint lithography (NIL) is a simple, high throughput and low cost method for the fabrication of micro- and nano-scale patterns. The fabrication process of the PMMA micro pillars on QCM surface is illustrated in FIG. 1, and comprises four sequential steps: (1) Preparation of SU-8 mother mold; (2) Preparation of PDMS transfer mold; (3) Filling mold with PMMA; (4) Thermal imprinting PMMA on QCM.

Step 1 Preparation of SU-8 Mother Mold

SU-8 is an epoxy-based negative photoresist having excellent mechanical properties and chemical resistance. SU-8 3000 series (MicroChem) was used to generate mother mold of NIL. The SU-8 films with different thickness were spin coated and micron sized holes were fabricated with conventional photolithography method.

Step 2 Preparation of PDMS Transfer Mold

PDMS (Sylgard 184, Dow Corning) was utilized as the mold material for NIL process since it is a low-cost silicone elastomer with a low surface energy which makes it well suitable for mold release during NIL process. PDMS precursor and cross-linker was fully mixed with a weight ratio of 10:1. The mixture was casted onto the SU-8 mother mold and degassed in vacuum for 30 minutes to remove the entrapped gas in the cavities. Then it was cured at 75° C. for 2 hours.

Step 3 Filling Mold with PMMA

PMMA is a transparent thermoplastic with small coefficient of thermal expansion and pressure shrinkage and has been widely used in NIL process. In this step, PMMA solution was prepared by dissolving a measured amount of PMMA with molecular weight of 120,000 (purchased from Sigma-Aldrich) into 2-Ethoxyethyl Acetate (purchased from Sigma-Aldrich) at 50° C. with stirring, and a transparent solution of 20 wt. % was obtained. Then a glass syringe was used to place several drops of PMMA solution on the PDMS transfer mold and wait for 1 minute until the solution flow into the microscale holes of PDMS mold. After this, the PDMS mold with PMMA solution was spun at 3000 rpm for 30 seconds to 1 minute to get a uniform PMMA layer. Then, the PDMS mold coated with PMMA was heated up on a hotplate at 100° C. for 5 minutes to evaporate all of the solvent.

Step 4 Thermal Nanoimprinting of PMMA on QCM

The imprinting process was conducted on a nanoimprinting machine (Nanonex 2600, Nanonex, N.J.). The pre-cleaned QCM and PDMS/PMMA pair was loaded into the chamber with a piece of silicon wafer as a support. The sample was pre-imprinted with pressure of 10 Psi at 120° C. (glass transition temperature: 105° C.), and then imprinted with pressure of 20 Psi at 180° C. for 2 minutes. The sample was cooling down to 45° C. with setting pressure of 20 Psi. After releasing the PDMS mold from QCM, the PMMA pillars (FIG. 2) was transferred onto QCM.

Characterization of Micropillars

The PMMA micropillars were characterized by a field emission scanning electron microscope (SEM, JSM-7401F) with an acceleration voltage of 5 kV. The heights of patterns were measured by the Optical Profilers (Wyko NT2000, Veeco Instruments).

Figure 2B:
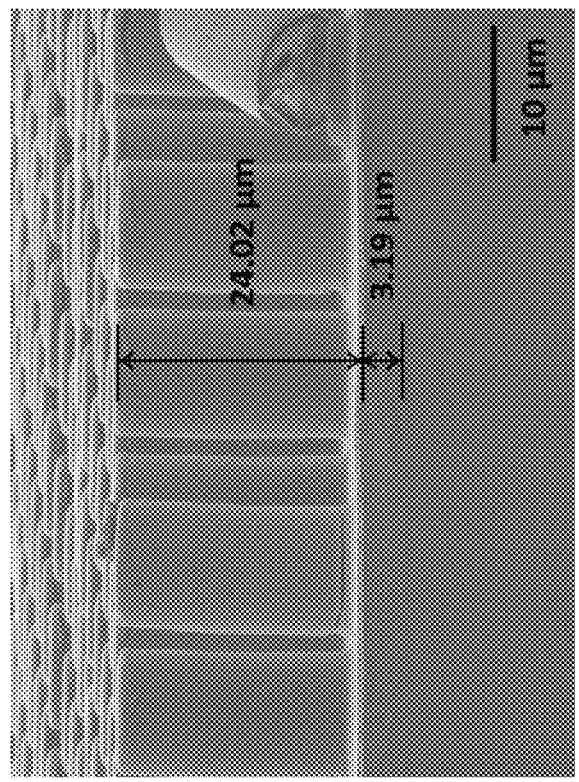
FIG. 2B is a side view of a PMMA micropillar array.
Figure 2A:
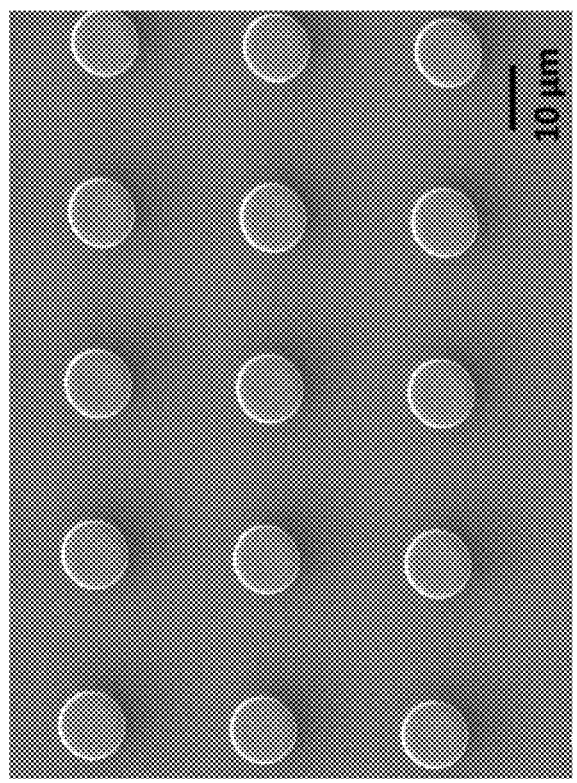
FIG. 2A is a top view of a PMMA micropillar array.

The top and side views of PMMA micropillar array are shown in FIG. 2A and FIG. 2B, respectively. It is worth noting that vertical side walls of pillars are critical for the mold releasing during NIL process. The designed pattern size was 10 μm in diameter compared to 9.86 μm measured from SEM.

Figure 2C:
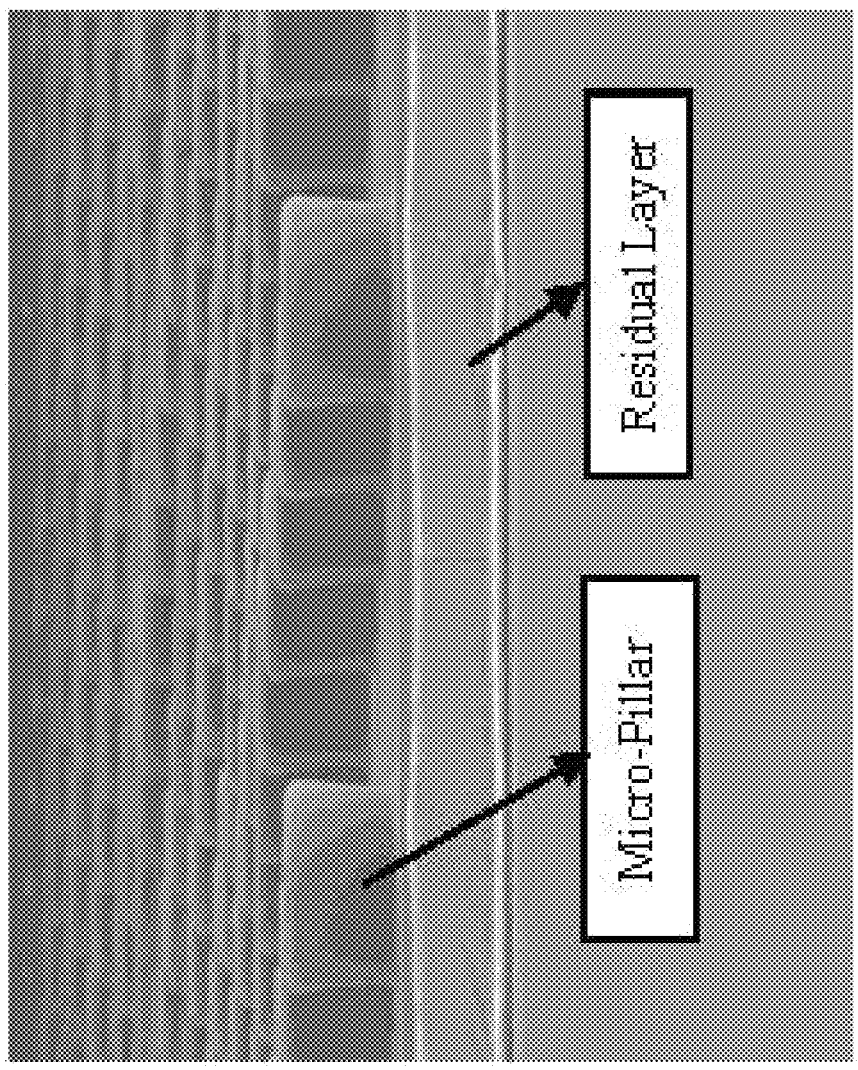
FIG. 2C is an SEM image of the micro-pillar layout and the residual layer.

FIG. 2C is an SEM image of the micro-pillar layout and the residual layer. A residual layer of a few microns will be formed during the fabrication process, T-NIL of micropillars as illustrated in FIG. 2C.

Figure 2D:
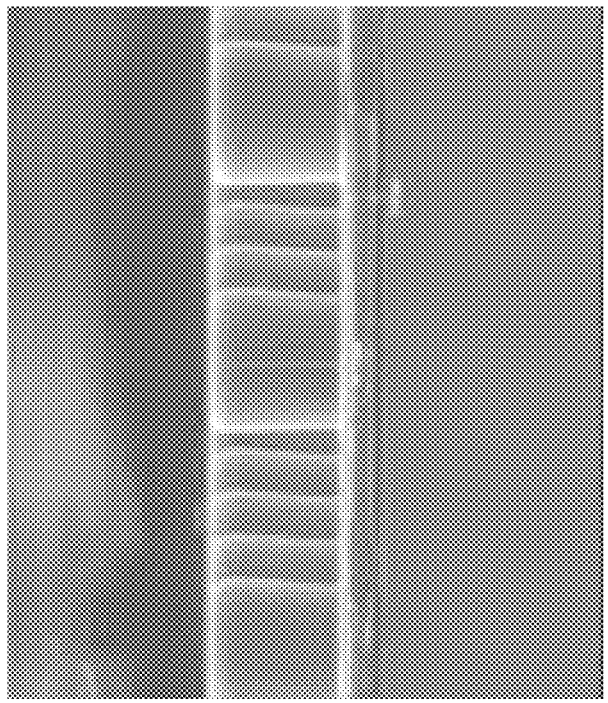
FIG. 2D is an SEM image of micro-pillars having a height of 5 microns.

FIG. 2D is an SEM image of micro-pillars having a height of 5 microns.

Figure 2E:
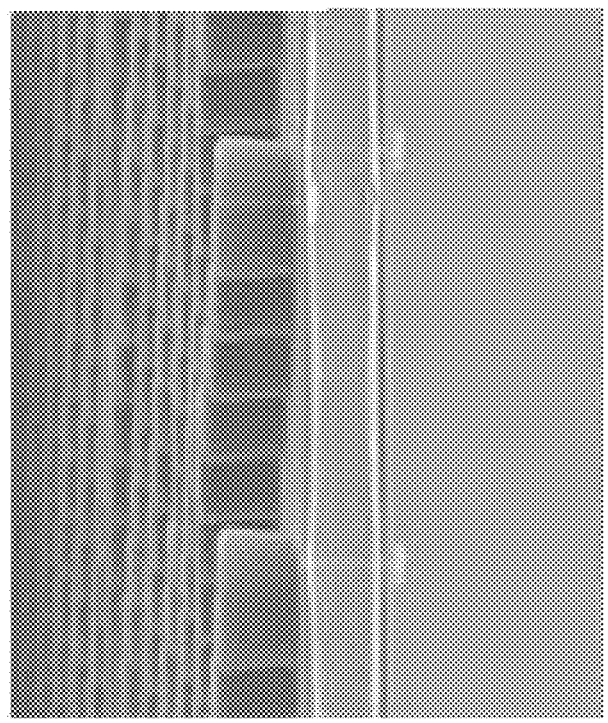
FIG. 2E is an SEM image of micro-pillars having a height of 10 microns.
Figure 3C:
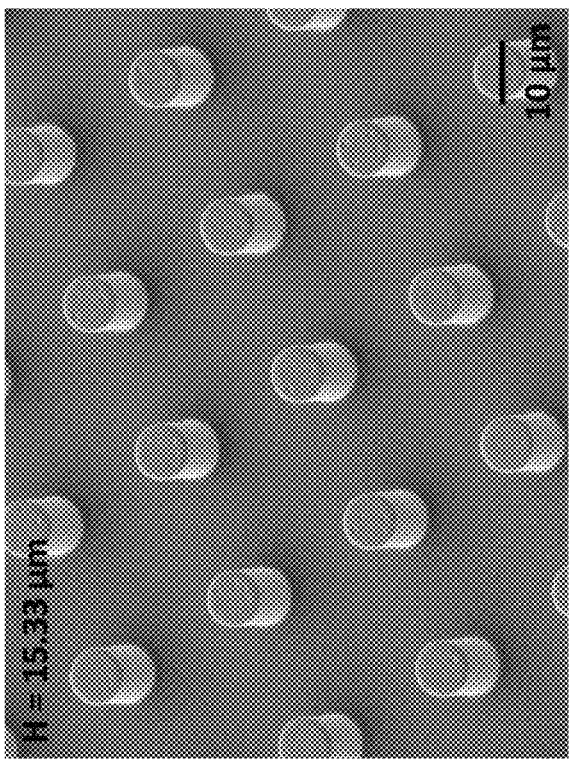
Figure 3D:
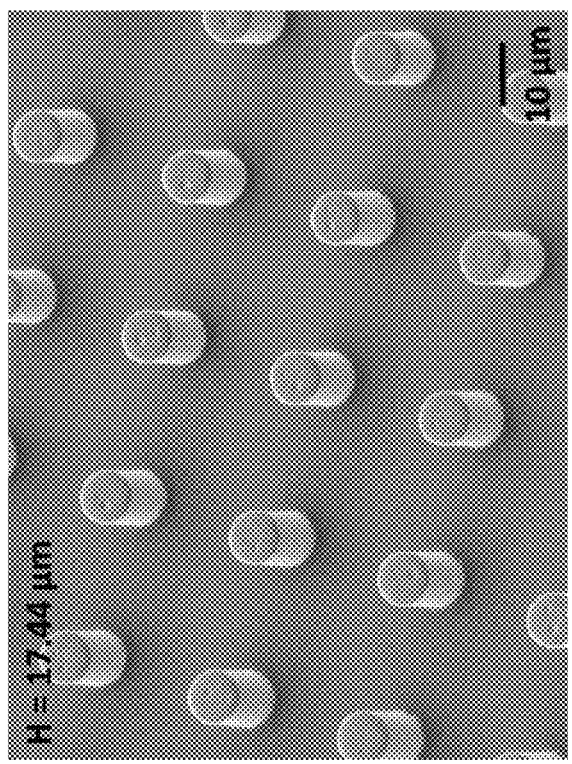
Figure 3F:
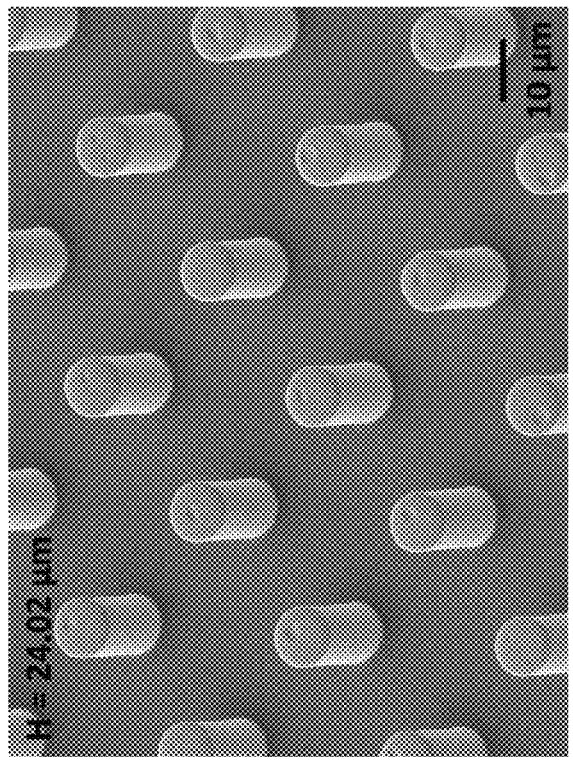
Figure 3E:
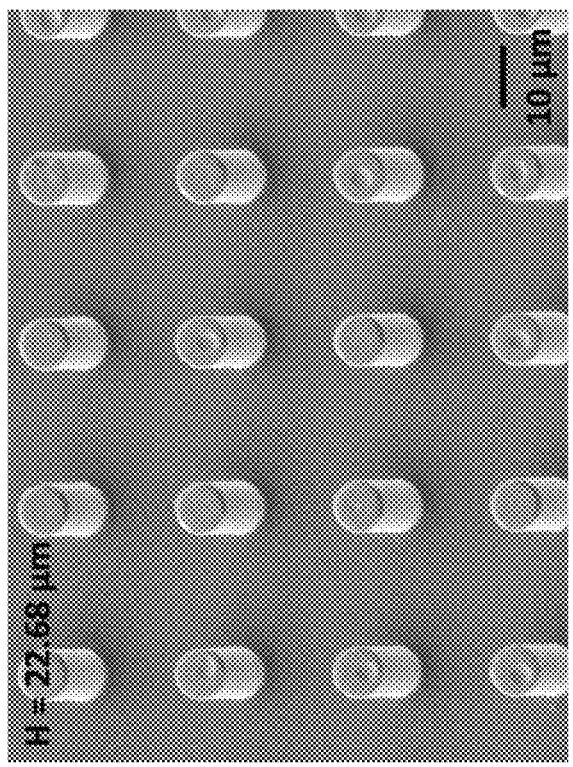

FIG. 2E is an SEM image of micro-pillars having a height of 10 microns.

FIG. 3A through FIG. 3F are images of microstructure patterned PMMA surface with various heights. The heights are respectively 5.92 μm, 9.65 μm, 15.33 μm, 17.44 μm, 22.68 μm and 24.02 μm) at an angle of 20 degree under SEM.

A thin residual layer (thickness: 3.19 μm) (FIG. 3A through FIG. 3F) can be seen at the bottom of the PMMA pillars after thermal nanoimprinting. This residual layer help improve the adhesion of pillars to gold surface of QCM, but it need to be carefully controlled since a thicker PMMA layer will lead to large damping of signal. The thickness of residual layer can be controlled by increasing the spinning speed in the process of PMMA filling and the imprinting pressure in the process of thermal imprinting.

There is no report so far to study the resonant characteristic of pillar structures on a QCM surface. This research is focused on the resonant characteristic of QCM sensor introduced by the coupling of patterned polymer pillar structures and QCM. The micron sized pillar array of Polymethyl methacrylate (PMMA) was fabricated on a QCM surface using NIL process. The coupled QCM-pillar system show a non-linear relationship between frequency shift and mass loading, which cannot be predicted by conventional theory. The QCM-pillar coupled resonant system exhibited an extremely high mass sensitivity when operated near the resonant point, which can be explained by "in-phase" or "out-of-phase" models. The new QCM-pillar coupled resonant system explored a new path to improve detection sensitivity of QCM for different applications. The QCM response to mass change-mass sensitivity of QCM is critical for different applications.

Figure 4A:
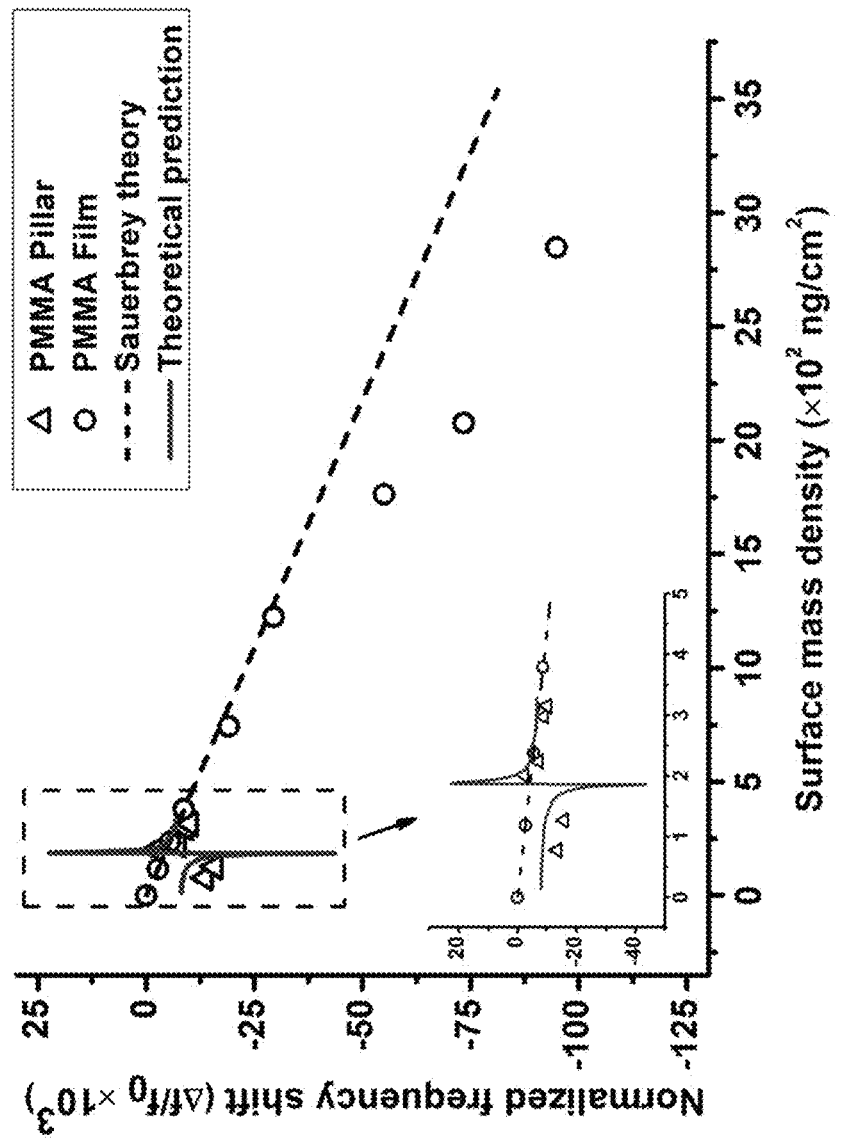
FIG. 4A is a graph showing a normalized frequency shift vs. surface mass density of the pillar-QCM system and conventional film QCM system.

FIG. 4A presents the experimental results of normalized frequency shift vs. surface mass density of the new coupled pillar-QCM system and conventional film-based QCM system, together with the prediction of resonant characteristic (solid curve) of twe pillar-QCM system based on two-degree of freedom vibration theory.

Figure 4B:
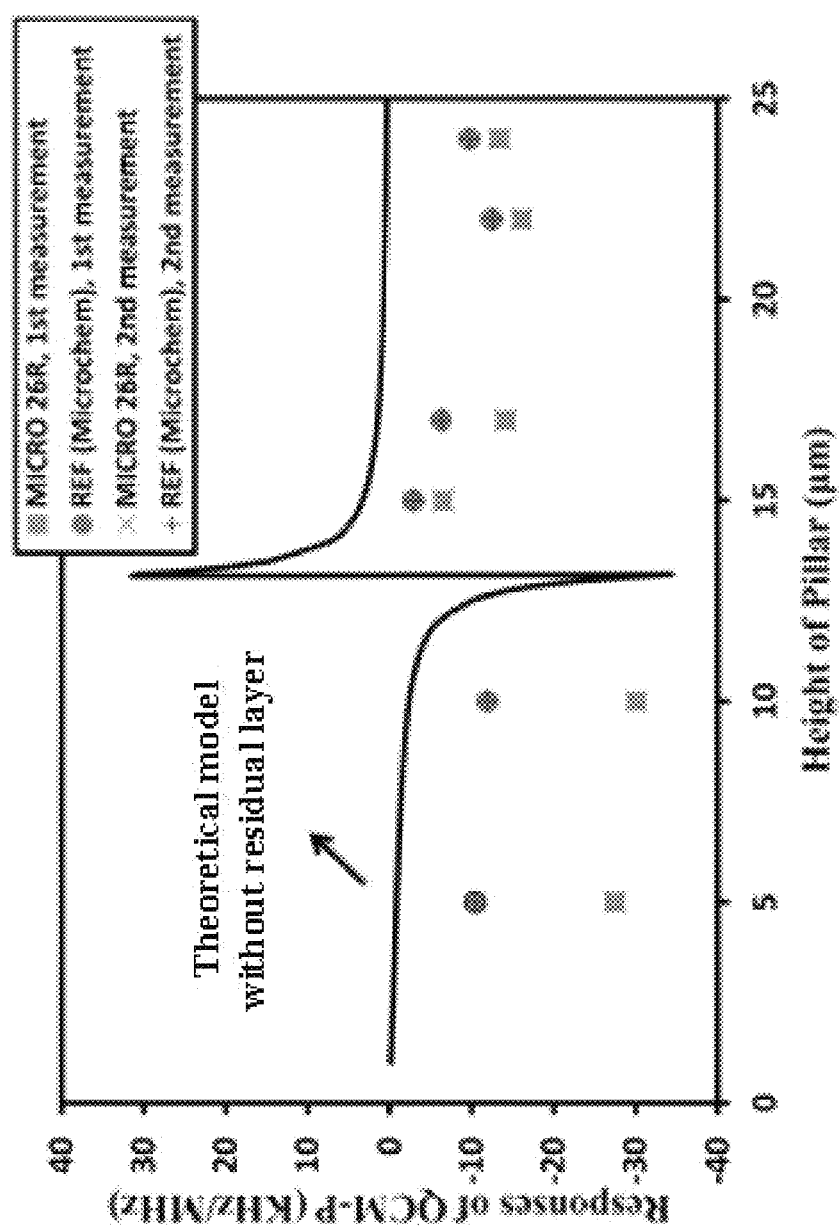
FIG. 4B is a graph showing the response of QCM-P devices versus heights of micro-pillars and comparison with theoretical model.

FIG. 4B presents the responses of QCM-P devices with two different PMMA samples. To facilitate the analysis, the resonant frequency shift of QCM-P device is normalized with the fundamental frequency of the bare QCM. The repeatability of the QCM-P response is checked as well. The results of theoretical modeling of QCM-P without considering the effect of residual layer are also plotted in the figure. As can be seen, the low polydispersity PMMA sample gives better sensor response. The actual response of QCM-P device is lower than the predicted one based on the theoretical model.

FIG. 4C and FIG. 4D illustrate the response of QCM-P devices in comparison with theoretical model which takes the resonant frequency shift due to the residual layer into account. A good agreement between the measurement and prediction verifies the effect of residual layer on QCM-P response. In addition, the QCM-P device with a low Pd (REF(MicroChem)) and the smallest residual layer thickness (t=2.48 μm) has the highest response while the response decreases with the increasing of the thickness of residual layer. It is believed that the discrepancies between the model prediction and experimental comes from two assumptions: 1) a rigid PMM thin film was assumed in the Sauerbrey theory (Eq. (B1)); 2) the residual layer thicknesses of all the pillars was the same for all heights.

Figure 4E:
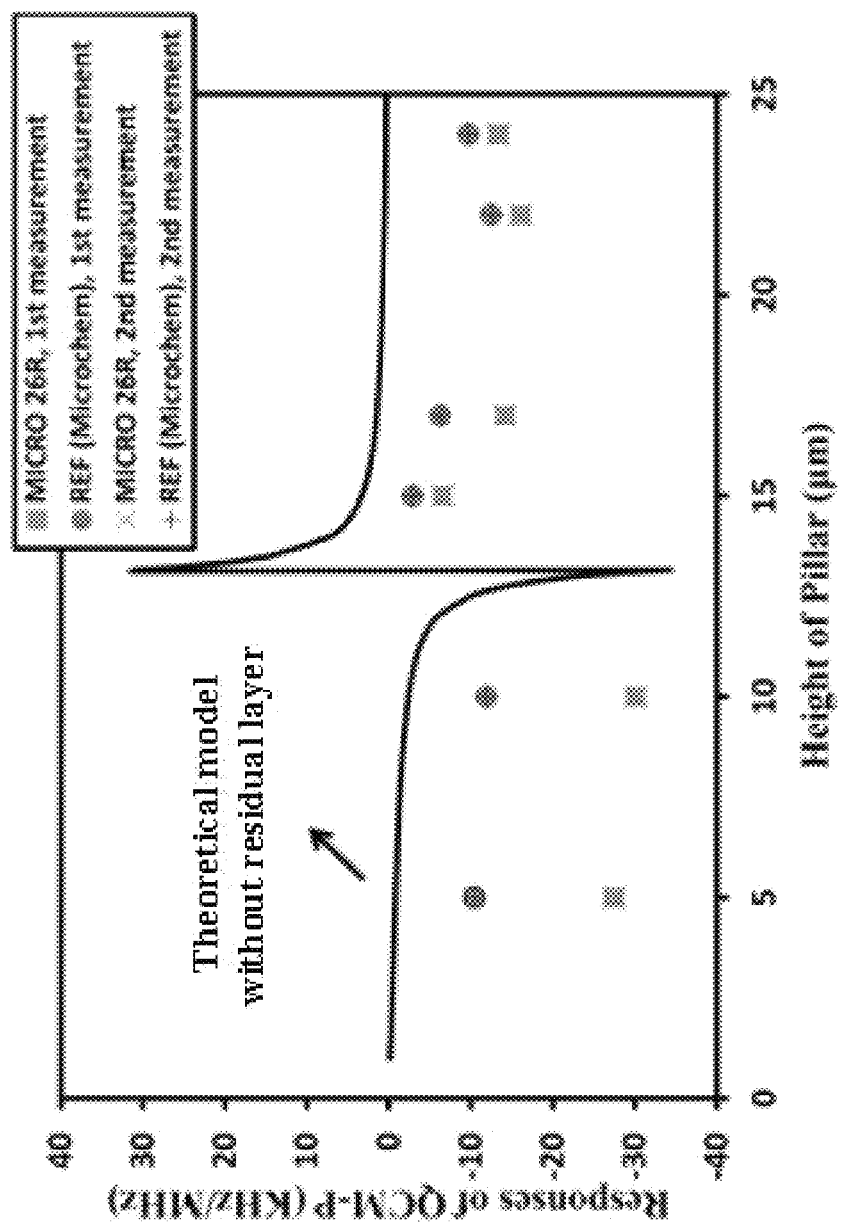
FIG. 4E is a graph showing the mass sensitivity of QCM-P devices with varying micro-pillar heights.

FIG. 4E shows the mass sensitivities of the QCM-P device predicted by the theoretical model, Eq. (B5), and conventional QCM predicted Sauerbrey theory, Eq. (B1). QCM-P surface mass density is obtained by dividing the residual layer and micro-pillar mass to the surface area of the bare QCM. As shown in the figure, several orders of magnitude improvement in mass sensitivity of QCM-P sensors can be achieved due to the two-degree of freedom coupled resonant system formed by micropillar and QCM substrate.

Figure 5:
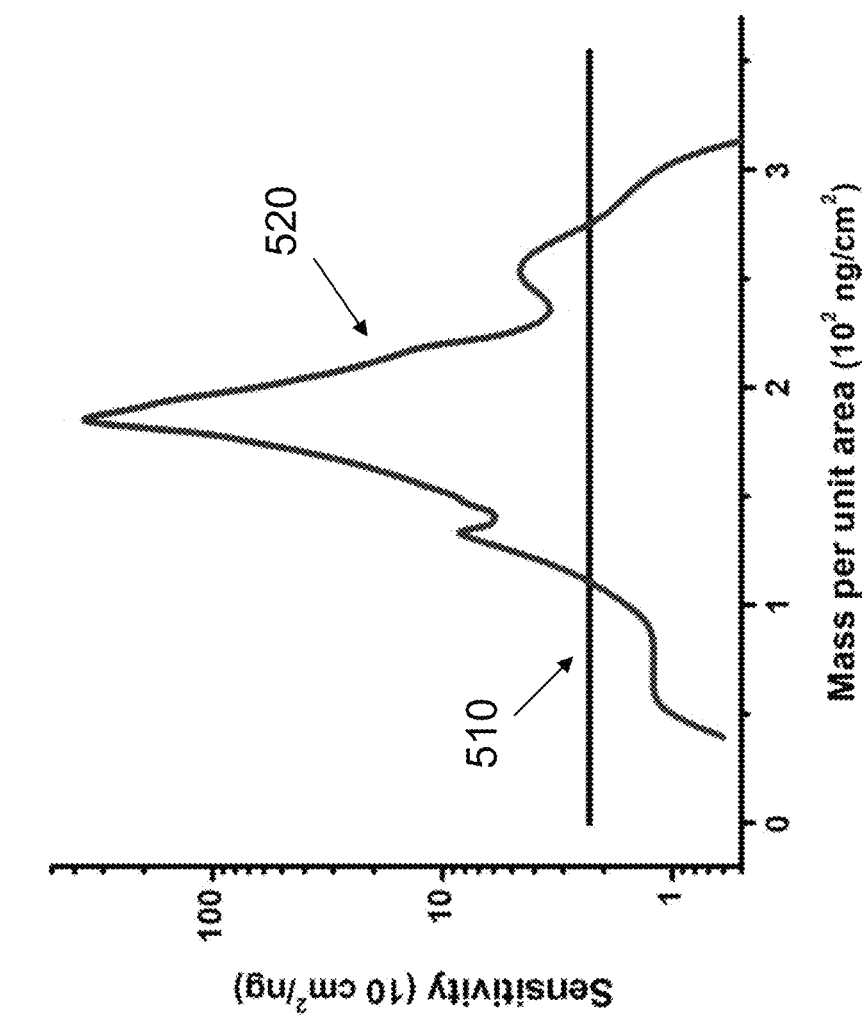
FIG. 5 is a graph that illustrates a comparison of the sensitivity of coupled pillar-QCM system (curve 510) with that of conventional film based QCM (line 510).

FIG. 5 is a graph that illustrates a comparison of the sensitivity of coupled pillar-QCM system (curve 510) with that of conventional film based QCM (line 510). FIG. 5 reports the improvements in mass sensitivity of coupled system over conventional film QCM system by several orders of magnitude when the system is operating near the new resonant frequency.

Figure 6:
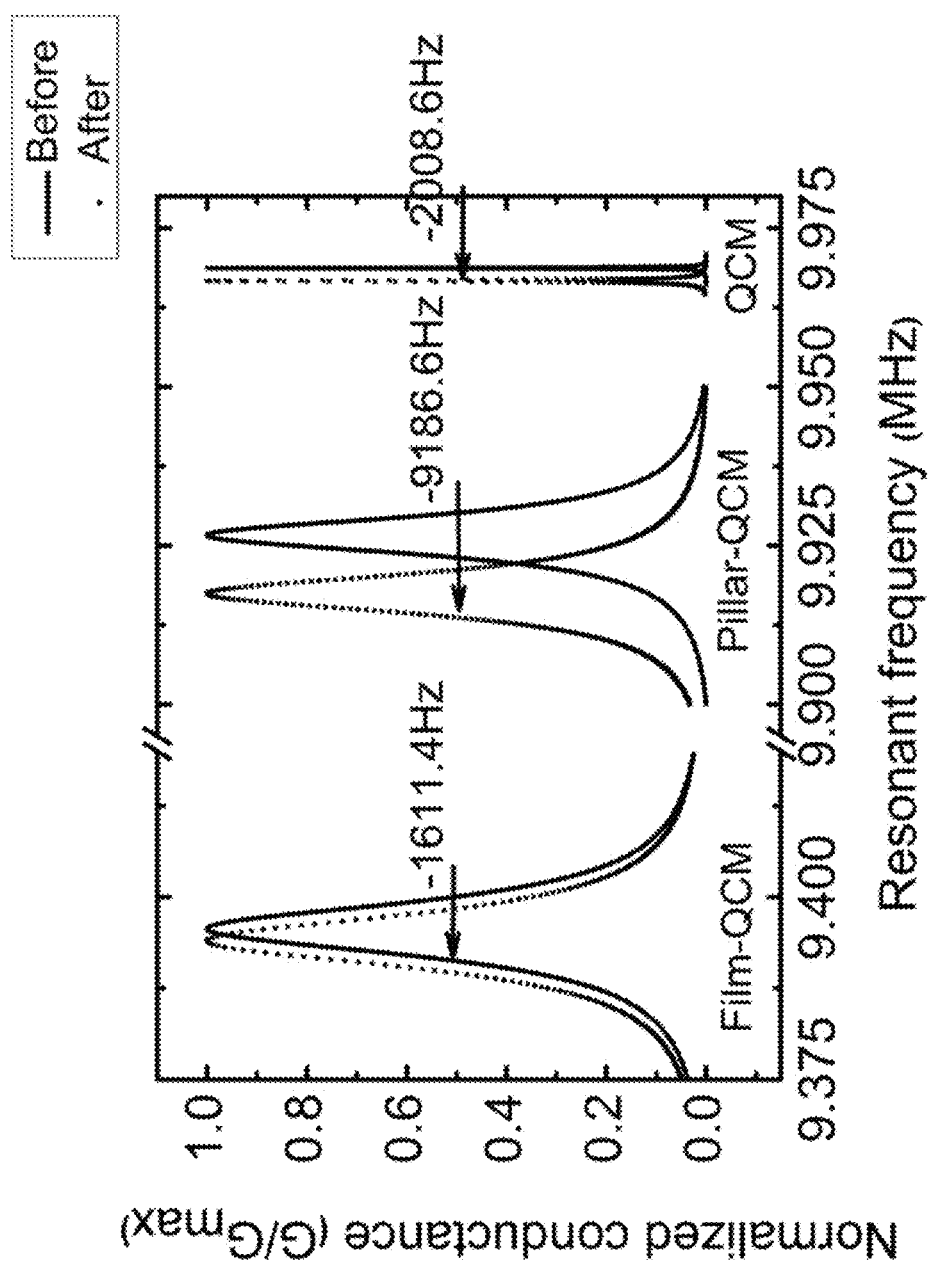
FIG. 6 is a graph showing resonant frequency shifts of film-based QCM, pillar-based QCM and bare QCM due to the mass loading of CVD-coated PFOTS monolayer.

The high mass sensitivity of QCM-micropillar coupled systems is demonstrated by detecting a monolayer of 1H, 1H, 2H, 2H-perfluorooctyl-trichlorosilane (PFOTS, >97%, Fluka). During the experiment, three QCM devices—QCM with PMMA micropillar (H=15.33 μm), QCM with PMMA film (H=14.95 μm) and bare QCM (used as reference)—were coated with a PFOTS monolayer using chemical vapor deposition (CVD) method. The frequency shift results are shown in FIG. 6. Compared to the frequency shift of −2008.6 Hz for bare QCM and −1611.4 Hz for QCM with film, a frequency shift of −9186.6 Hz for QCM with micropillars was achieved. An increase of 357% has been obtained using QCM-micropillar coupled system.

FIG. 6 is a graph that illustrates the resonant frequency shifts of film-based QCM, pillar-based QCM and bare QCM due to the mass loading of CVD-coated PFOTS monolayer.

Other materials and nano-scale features have been combined with QCM for humidity detection, including ZnO nanospheres of 680 nm diameter, ZnO nanorods of 300 nm diameter and 1.0 μm length, carbon nanotubes with a diameter of 30~50 nm and length of 20.0 μm, Bacterial cellulose nanofibers of 30~70 nm diameter, PMMA porous film. They are compared with our work using PMMA (Mw~950 K) micropillars with a height of 17.44 μm as shown in FIG. 7.

The significant increase in sensing area enabled by nano-scale features has greatly improved QCM response, such as a frequency shift of −850 Hz/MHz from porous PMMA film coated QCM. However, QCM-Micropillars device increases the frequency shift up to −1692.14 Hz/MHz, almost twice that of the porous PMMA film. The ease of fabrication and potential in large scale manufacturing shown in this report make QCM-Micropillars devices very attractive for humidity and other trace level detection of chemicals.

Figure 7A:
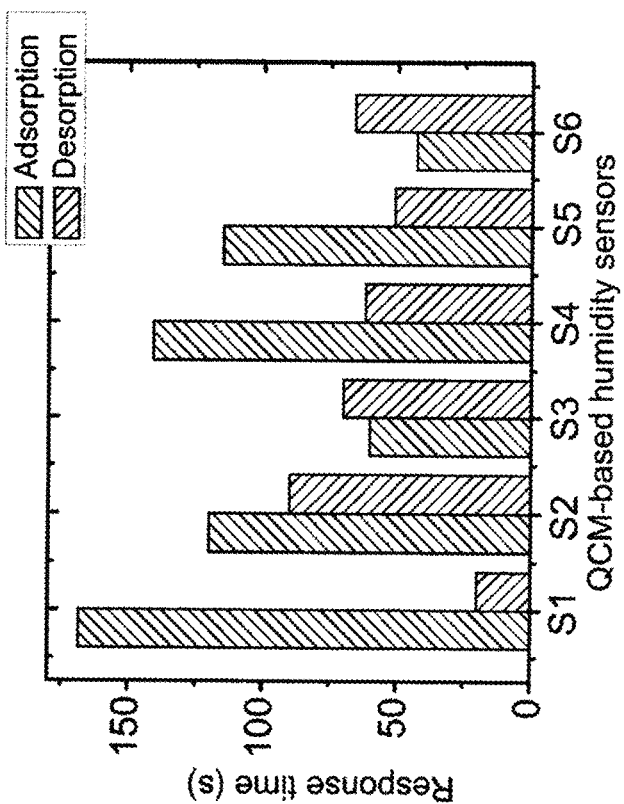
FIG. 7A is a graph illustrating a comparison of a QCM-Micropillar device with the other QCM-based humidity sensors showing normalized frequency shifts.

FIG. 7A is a graph illustrating a comparison of a QCM-Micropillar device with the other QCM-based humidity sensors showing normalized frequency shifts.

Figure 7B:
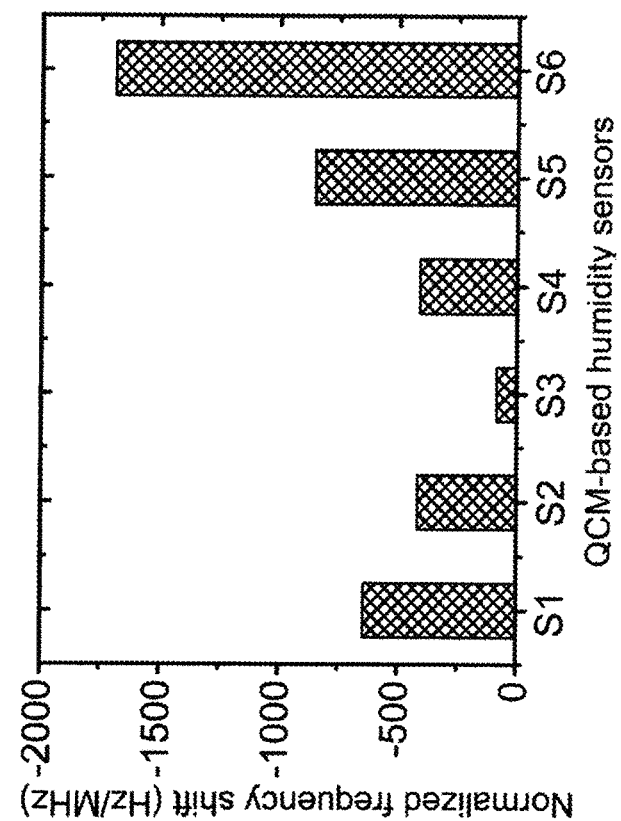
FIG. 7B is a graph illustrating a comparison of a QCM-Micropillar device with the other QCM-based humidity sensors showing response time.
Figure 8:
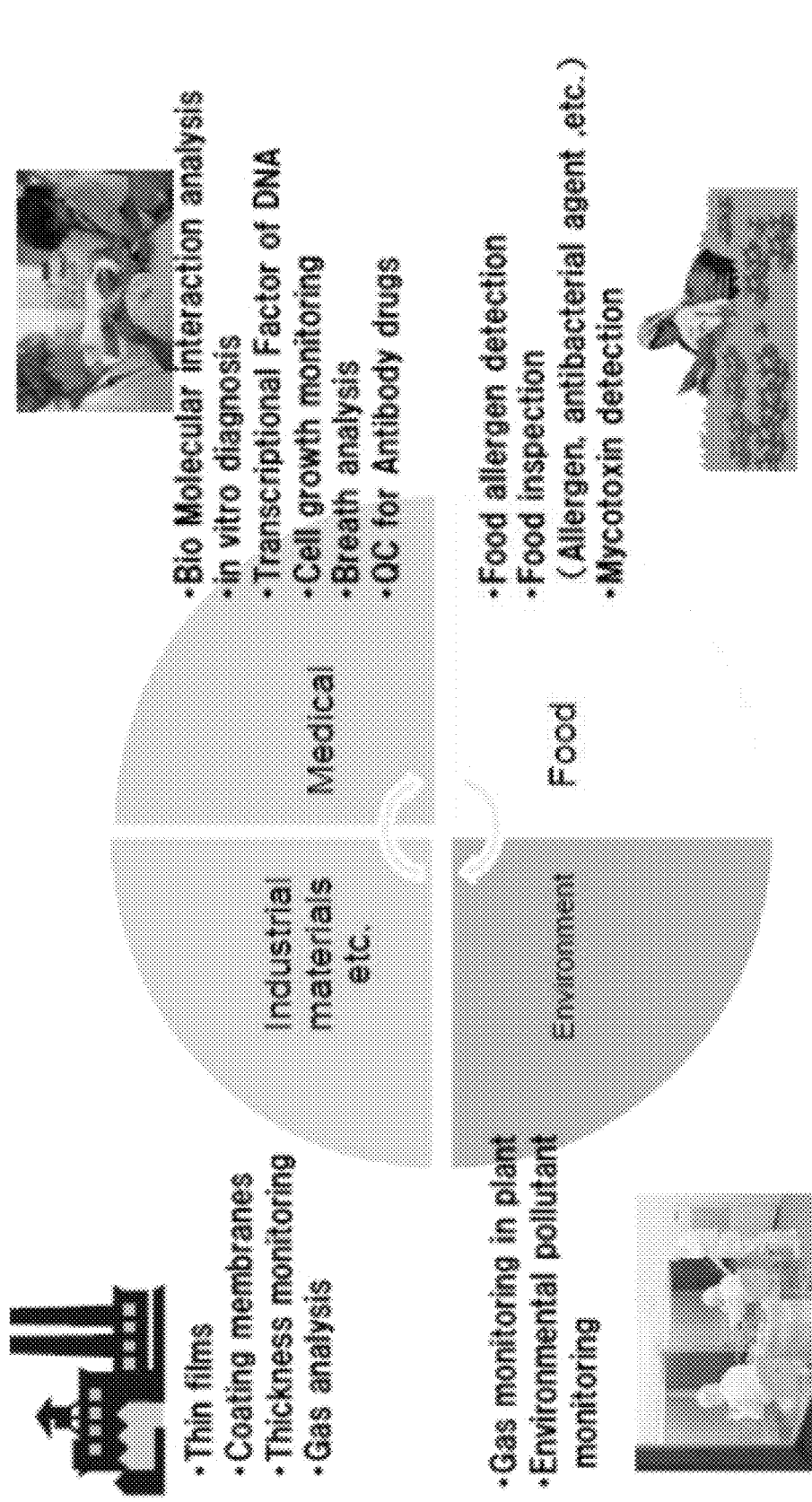
FIG. 8 illustrates some of the expected fields of use of the invention.

FIG. 7B is a graph illustrating a comparison of a QCM-Micropillar device with the other QCM-based humidity sensors showing response time. FIG. 8 is a diagram illustrating various application of the invention.

In the figures, S1 denotes ZnO nanospheres, S2 denotes ZnO nanorods, S3 denotes Carbon nanotubes, S4 denotes Bacterial cellulose nanofibers, S5 denotes PMMA porous film, S6 denotes PMMA (Mw~950K) micropillars of 17.44 μm pillar height.

Applications

It is believed that the systems and methods of the invention can have application in a wide variety of fields including, but not limited to applications in gas and liquid sensors, biosensors, thin film deposition measurement, affinity of molecules (proteins) to surfaces detection, interactions between biomolecules, probing solid/liquid interface, and viscoelastic properties of polymers.

FIG. 8 illustrates some of the expected fields of use of the invention. It is believed that the invention as embodied in coupled micropillars and QCM resonant devices can improve the sensitivity of all QCM based sensors.

Theoretical Model of QCM-P

Figures 9A, 9B:
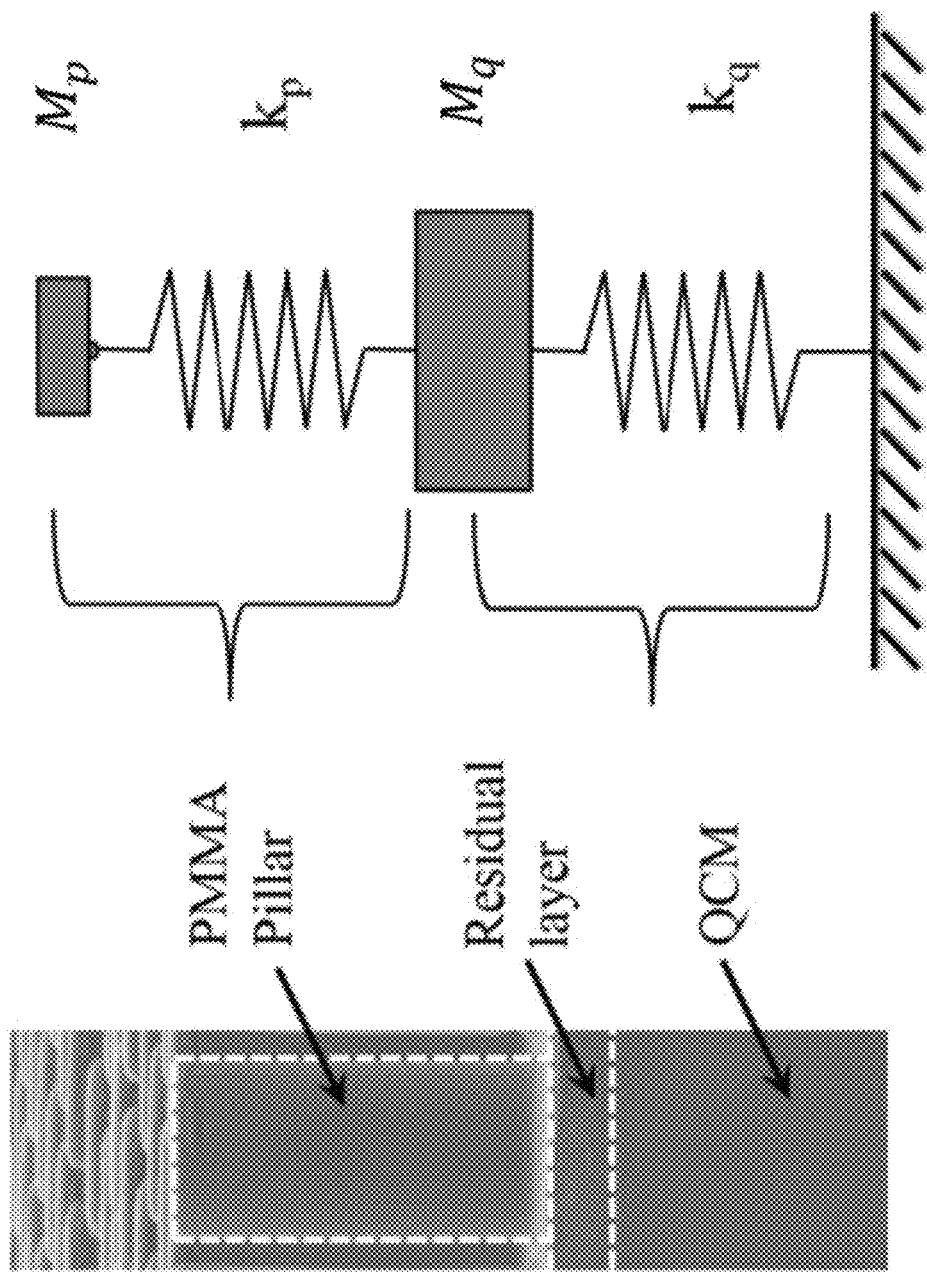
FIG. 9A is a diagram of a QCM-P device having two degrees freedom.
FIG. 9B is an illustrative circuit diagram of the two degrees freedom system for the QCM-P device illustrated in FIG. 9A.

FIG. 9A is a diagram of a QCM-P device having two degrees freedom.

FIG. 9B is an illustrative circuit diagram of the two degrees freedom system for the QCM-P device illustrated in FIG. 9A.

For a QCM-P device operating in the air, illustrated by FIG. 9A, the damping effect caused by the viscosity of environment is negligible. As a result, the PMMA micropillar and QCM substrate can be modeled as two mass-spring systems connected in series as illustrated in FIG. 9B.

In this model, QCM substrate is considered as the main resonator with mass ($M_q$) and a spring with force constant ($K_q$). Based on the resonant frequency of QCM itself, the force constant of QCM can be obtained as:

$$K_q = m\omega^2, \omega = 2\pi f_0 \quad (4)$$

Furthermore, a PMMA micro-pillar is treated as a mass ($M_p$) and a spring with the force constant ($K_p$). The resonant frequency of micro-pillar ($f_p$) is obtained as:

$$f_p = \frac{3.52}{2\pi H^2} \sqrt{\frac{EI}{M}} \quad (5)$$

where, H is the height of the micro-pillar, E is the Young's modulus, I is the moment of inertia and $\dot{M}$ is the mass of micro-pillar per unit length. Based on value of the resonant frequency of micro-pillar ($f_p$), the equivalent force constant ($K_p$) of micro-pillar is obtained.

A relationship between displacement of QCM and micro-pillar is established with the Newton's second law given by:

$$\begin{bmatrix} M_q & 0 \\ 0 & M_p \end{bmatrix}\begin{pmatrix} \ddot{x}_1 \\ \ddot{x}_2 \end{pmatrix} + \begin{bmatrix} k_q+k_p & -k_p \\ -k_p & k_p \end{bmatrix}\begin{pmatrix} x_1 \\ x_2 \end{pmatrix} = \begin{pmatrix} 0 \\ 0 \end{pmatrix} \quad (6)$$

where $x_1$ and $x_2$ represent the displacements of the QCM and PMMA micro-pillar, respectively. The resonant frequency of the system can be obtained as:

$$f = \frac{1}{2\pi}\sqrt{\frac{1}{2}\left(\frac{k_q}{M_q}+\frac{k_p}{M_q}+\frac{k_p}{M_p}\right) \pm \frac{1}{2}\left[\left(\frac{k_q}{M_q}+\frac{k_p}{M_q}+\frac{k_p}{M_p}\right)^2 - 4\frac{k_q}{M_q}\frac{k_p}{M_p}\right]^{1/2}} \quad (7)$$

It should be noticed that the response of QCM-P in Eqn. (7) doesn't consider the effect of residual layer.

Theoretically, a thin film deposited on the surface of a QCM will behave as an ideal mass layer if it is sufficiently thin and rigid so that it moves simultaneously with the QCM. This condition is judged by the value of acoustic phase shift φ across the film. The acoustic phase shift φ is calculated as:

$$\varphi = \omega t \sqrt{\frac{\rho}{G}} \quad (8)$$

where ω is the resonant frequency of QCM and ρ, G and t are the density, shear modulus and thickness of the residual layer, respectively. When the phase shift φ is small, i.e. φ<π, the resonant frequency shift of QCM due to the residual layer is obtained as:

$$\frac{\Delta f}{f_0} = -\frac{\rho_s}{h_s \rho_q} \quad (9)$$

where $f_0$ is the resonant frequency of QCM, $\rho_s$ is the surface mass density of residual layer, $h_s$ and $\rho_q$ are the thickness and density of the quartz, respectively.

Observed and Theoretical Results

Two PMMA pillar samples with similar molecular weight but different polydispersity (Pd) were prepared. Polydispersity is defined as the ratio of mean molecular weight to the number molecular weight of a specific polymer. The closer the polydispersity approaches the value of one, the narrower is the molecular weight distribution.

The molecular information of PMMA used in the experiment is listed in Table 1.

TABLE 1

Information of PMMA samples.

| Sample | $M_n$ | $M_w$ | Pd = $M_w/M_n$ |
|---|---|---|---|
| REF (MicroChem) | 41202 | 76916 | 1.87 |
| Micro 26R | 25162 | 77955 | 3.10 |

To measure the thickness of residual layer, the PMMA micro-pillars listed in Table 1 were fabricated on glass substrates using T-NIL. Both profilometer (DekTak) and SEM were used to measure the thickness of residual layer. For the SEM method, the glass piece was broken and then a sputter machine (Denton-Vacuum Desk IV) was employed to deposit a thin layer of gold (3 nm) to increase the conductivity of PMMA and prevent the charging effect.

Tables 2 and 3 contain information of the heights of micro-pillars and residual layer measurements using Dek-Tak and SEM, respectively.

TABLE 2

Comparison between residual layer and height of micro-pillar measurements using Dektak machine.

| Height of Pillar (μm) | MICRO-26R | | REF (MicroChem) | |
|---|---|---|---|---|
| | Height of Pillar (μm) (Measurement) | Residual layer (μm) | Height of Pillar (μm) (Measurement) | Residual layer (μm) |
| 5 | 6.60 | 7.05 | 6.15 | 4.20 |
| 10 | 10.35 | 6.30 | 10.33 | 4.48 |

TABLE 3

Comparison between residual layer and height of micro-pillar measurements using SEM method.

| Height of Pillar (μm) | MICRO-26R | | REF (MicroChem) | |
|---|---|---|---|---|
| | Height of Pillar (μm) (Measurement) | Residual layer (μm) | Height of Pillar (μm) (Measurement) | Residual layer (μm) |
| 5 | 6.34 | 6.10 | 5.87 | 2.89 |
| 10 | 9.68 | 5.22 | 10.00 | 2.48 |
| 22 | 30.66 | 5.16 | 22.88 | 4.03 |
| 24 | 24.80 | 6.60 | 19.69 | 3.56 |

It is apparent that the residual layer thickness for REF (MicroChem) PMMA sample with a lower Pd is smaller than that of Micro 26-R PMMA sample. The calculation of acoustic phase shift φ across residual layer using Eqn. (8) is shown in Table 4.

TABLE 4

Acoustic phase shifts for different residual layer thickness.

| Thickness (μm) | | | | | | | |
|---|---|---|---|---|---|---|---|
| 2.48 | 2.89 | 3.56 | 4.03 | 5.16 | 5.22 | 6.1 | 6.6 |
| φ | | | | | | | |
| 0.13 | 0.15 | 0.19 | 0.21 | 0.26 | 0.27 | 0.32 | 0.35 |

As the acoustic phase shifts are much smaller than Pi (φ<π), the residual layer is treated as a thin and rigid mass layer which moves synchronously on the QCM surface [2]. As a result, the resonant frequency shift of QCM-P due to the residual layer can be obtained using Eqn. (9) and is added into the frequency calculation (Eqn. (7)).

The effects of residual layer and polydispersity index (Pd) of PMMA on the responses of the pillar-based QCM (QCM-P) devices were measured. QCM-P sensors were fabricated using thermal nano-imprinting method. Both theoretical and experimental results show that the mass sensitivity/frequency shift of QCM-P devices is enhanced significantly when the height of the pillar approaches the critical height of the micro-pillar. The results show the residual layer behaves as an additional mass and significantly reduces the frequency shift of QCM-P sensor while a low polydispersity of PMMA improves the sensor responses. The results confirmed that PMMA with a lower Pd has larger resonant frequency response in comparison to the PMMA with a higher Pd. Theoretical results show that with increasing the thickness of residual layer, the response of QCM-P decreases.

Measurement Apparatus

Figure 10:
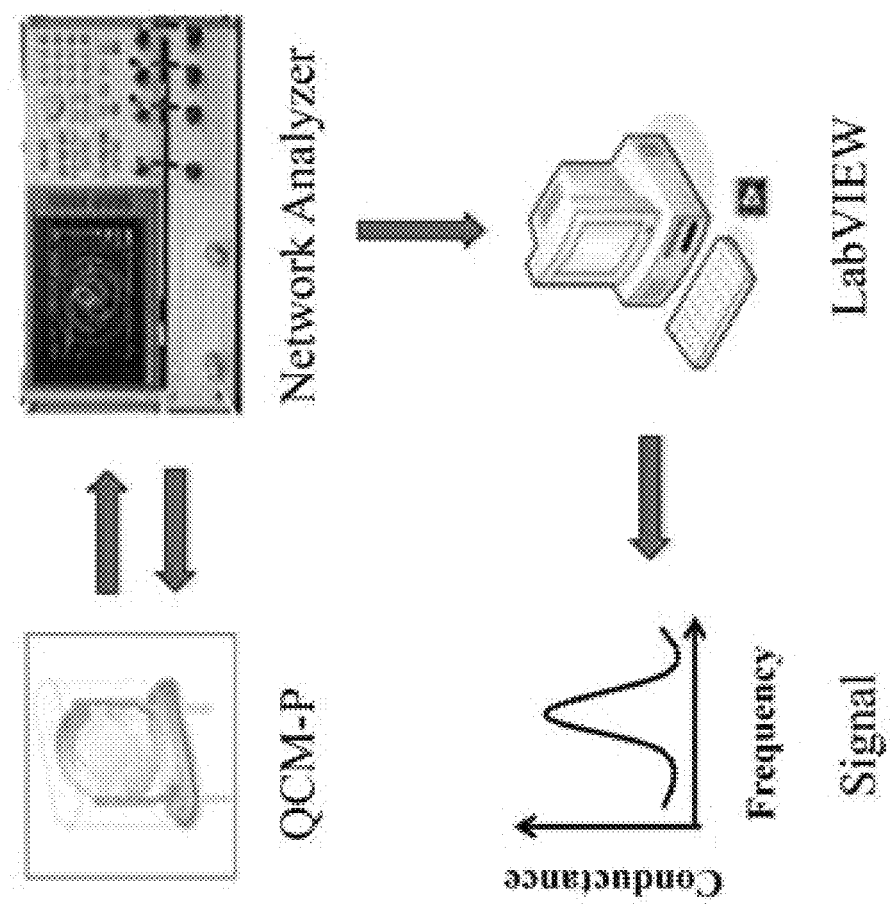
FIG. 10 is a schematic diagram of the QCM-P measurement system.

To measure the frequency shift of the QCM-P, an experimental setup consisting of a network analyzer (HP8753C and 85046-A S-Parameter test set), a data acquisition (DAQ) system, a built-in LabVIEW program (National Instruments) and the QCM-P device were built. The QCM-P devices used in this study were fabricated on 10 MHz bare QCMs. The network analyzer actuates the QCM-P device while recording the reflected signal created by QCM-P device. In the end, the reflected signal is analyzed by an in-house LabVIEW program. FIG. 10 displays the schematic of the measurement apparatus.

Dropwise Condensation Data

Dropwise condensation (DWC) on hydrophobic surfaces is attracting increasing attention due to its great potential in different industrial applications, such as steam-based power generation, water desalination, and anti-/de-icing of turbine blades. The lack of direct measurement technologies to quantify the drop dynamics of DWC significantly hinders the progress toward a full understanding of the thermal and mass transport mechanism on these surfaces. This work reports a novel quartz crystal microbalance (QCM) based method to quantitatively analyze the droplet dynamics during different condensation states such as Cassie, Wenzel and partial wetting states. The micro-pillar based hydrophobic and hydrophilic surfaces for different condensation processes were fabricated by a combined nanoimprinting lithography (NIL) technology and chemical surface treatment. The frequency shifts of the QCM device and microscopic observation clearly manifest different characteristics of condensation states such as filmwise, Wenzel, and partial wetting condensations, as well as growth modes of droplets during these condensation processes. In addition, the transition between Cassie and Wenzel states has been determined using this technique. The developed QCM system provides a valuable tool for the dynamic characterization of condensation process on rough surfaces and effective surface design for dropwise condensation.

Water vapor condensation on solid surfaces is crucial to a wide range of potential industrial applications, such as steam-based power generation, water desalination, water harvesting, thermal management and anti-fog surfaces. Dropwise and filmwise condensations are the two major condensation modes when a vapor contacts a cool surface whose temperature is below its saturation temperature. A liquid film, which is formed on the solid surface during the filmwise condensation, usually acts as a barrier both for heat transfer and mass transfer, and thereafter results in a low heat transfer coefficient (HTC). However, dropwise condensation (DWC) with the generation of small droplets ranging from a few micrometers in diameter to agglomerations visible to eyes, was first recognized by Schmidt et al. and is a favorable condensation mode in industrial applications offering order of magnitude larger condensation efficiency than those for filmwise condensation. DWC has been reported to produce heat transfer coefficients (HTC) 5 to 7 times of those found in filmwise condensation under lab conditions.

Different micro/nanostructure based superhydrophobic surfaces have been intensively designed to achieve dropwise condensation in the last decades. Numbers of fabrication methods have been reported to produce biomimetic roughness-induced hydrophobic surfaces such as plasma-enhanced chemical vapor deposition, conventional photolithography and etching, self-assembled monolayers on nanostructures, template-based extrusion, electrospinning and some other techniques such as a slippery liquid-infused porous surface, and layer-by-layer deposition. Some of these surfaces have shown a great potential to further improve the efficiency of dropwise condensation.

Figure 11A:
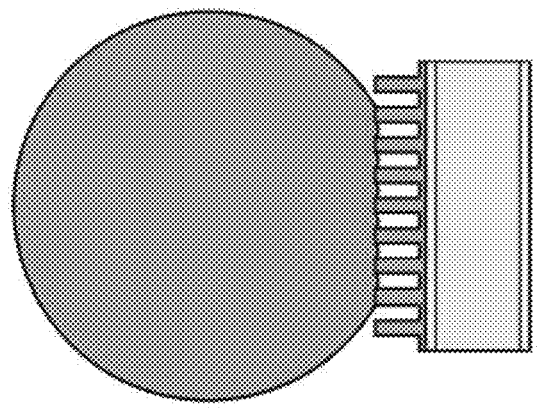
FIG. 11A is a diagram of a drop placed on a rough surface in the Cassie state.
Figure 11B:
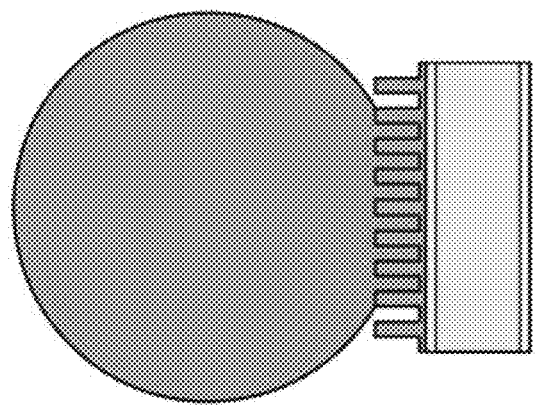
FIG. 11B is a diagram of a drop placed on a rough surface in the Wenzel state.

When a liquid drop is placed on a rough hydrophobic surface, two distinct wetting states could occur: Cassie state in which drop is suspended on the top of the roughness of the surface or Wenzel state where the liquid of the drop fills in the roughness without spreading, as shown in FIG. 11A and FIG. 11B.

Figure 11C:
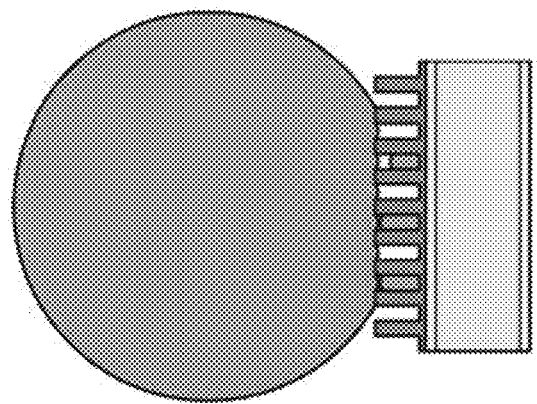
FIG. 11C is a diagram of a drop placed on a rough surface in a partial wetting state.

It should be pointed out that both Cassie and Wenzel state droplets could achieve a high contact angle of the drop while the liquid penetration only takes place for Wenzel state. During DWC process, one of the two wetting states may happen spontaneously depending on thermal, physical and chemical conditions of the surface or a partial wetting state-partial Cassie and partial Wenzel, (shown in FIG. 11C) could occur. The reason is that the nucleus (at a radius on the order of 1~10 nm) of dropwise condensation usually takes place in between roughness, and easily wet the cavities of the micro/nanoscale structures to form Wenzel drops while others occur on the top of the roughness and will form Cassie drops.

Some of the analyses of experimental results were supported by optical microscope or Environmental Scanning Electron Microscope (E-SEM). For example, Narhe RD and Beysens DA described sequential condensation stages on square shape micro-pillars. Dorrer C and Rühe J observed the transition from Wenzel to Cassie states by an optical microscope and a CCD camera. Rykaczewski illustrated the growth mechanism of individual microscale water droplets on a superhydrophobic surface with in-situ E-SEM. Through the experimental observation and interface free energy calculation, quantitative design guidelines for superhydrophobic surfaces intended for dropwise condensation applications were also developed. However, the resolution of optical systems (tens of microns) has severely limited the maximum size of droplets and time scale of the dynamics process that can be analyzed. Currently, the common approach adopted for DWC studies is based on an indirect method, in which the heat flux and temperature of the condensation surfaces are measured and presented in the form of either heat flux or heat transfer coefficient (HTC) vs. subcooling temperature.

There is a lack of a powerful tool to quantitatively evaluate wettability and dynamic process of dropwise condensation on a hydrophobic surface which can answer some critical questions such as: How much nucleation are taking place at the initial stage of condensation? Are the drops with high contact angles under Wenzel state or Cassie state? Is there any transition between Wenzel or Cassie states during dropwise condensation? What is the effect of wetting states on condensation? How long the hydrophobicity of a surface can be maintained during dropwise condensation?

Quartz crystal microbalance (QCM), is a simple, cost effective, high-resolution sensing device, relying upon piezoelectric effect to sense the mass loading change on its surface with an extremely high sensitivity (<10 ng/cm$^2$). QCM devices were also used to characterize the viscoelasticity of a wide variety of polymer materials. A QCM device was traditionally used in vacuum or in gaseous environment and the presence of a chemo-sensitive coating that interacts with target gas makes QCM highly sensitive to mass change. Since Nomura showed that a crystal material completely immersed in liquid can be driven to oscillate in a stable manner, the application of QCM has been extended to liquid phase environment. As the QCM devices can be utilized in both gaseous and liquid phase environments with a high sensitivity, there is a great potential for QCM devices to be used to study proposed condensation process.

As is described herein, the hydrophilic and hydrophobic surfaces were constructed through imprinting polymethyl methacrylate (PMMA) microscale pillar structures on 10 MHz QCM surfaces using nanoimprinting lithography (NIL) technology. The pillar surfaces were made superhydrophobic or superhydrophilic using different surface treatment. Either filmwise or dropwise condensation was achieved on these surfaces. Distinct frequency shift signals of QCM devices for filmwise and three dropwise condensations were captured by a frequency counter based measurement system. In addition, the transition from Wenzel to Cassie state was quantitatively observed on partial wetting hydrophobic micropillar surface.

Micro Pillar Design and Surface Preparation

By comparing the dimensionless energy, E* of a liquid wetting the pillar structures in Wenzel and Cassie states, the condensed droplet morphology can be determined as follows.

$$E^* = \frac{\cos\theta_a^{CB}}{\cos\theta_a^W} = \frac{-1}{r\cos\theta_a} \quad (10)$$

where r=1+πdh/l$^2$ is the dimensionless surface roughness, d and h are the diameter and height of the pillars, l is the center to center spacing between pillars. It is worth noting that when E* is greater than 1, the Wenzel state would be energetic favorable. However for 0<E*<1, Cassie would be more possible to occur. According to the interface free energy calculation and quantitative design guidelines, the dimensions of micro pillars were chosen and their static intrinsic and apparent contact angles were also measured (shown in Table 5).

TABLE 5

Dimension of micropillars, contact angle and dimensionless energy

| | Dimensions | | | | Contact angle (°) | | |
|---|---|---|---|---|---|---|---|
| | d (μm) | l (μm) | h (μm) | r | Intrinsic | Apparent | E* |
| S1(Bare QCM) | N.A. | N.A. | N.A. | 1 | 69 | 69 | −2.79 |
| S2(QCM-P) | 10 | 25 | 15 | 1.75 | 35 | 5 | −0.58 |
| S3(QCM-P) | 10 | 25 | 15 | 1.75 | 96 | 152 | 5.45 |
| S4(QCM-P) | 7 | 10 | 22 | 5.84 | 105 | 149 | 0.66 |

Figure 12A:
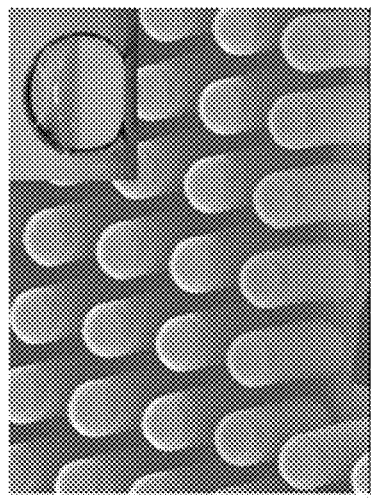
FIG. 12A is an SEM image of PMMA micro pillar arrays (tilted at 20°) for partial wetting condensation (S4).
Figure 12B:
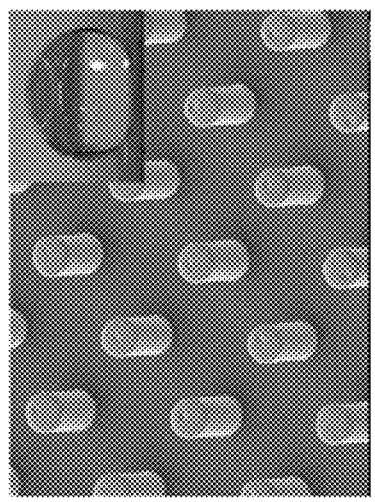
FIG. 12B is an SEM image of PMMA micro pillar arrays (tilted at 20°) for Wenzel wetting condensation (S3).
Figure 12C:
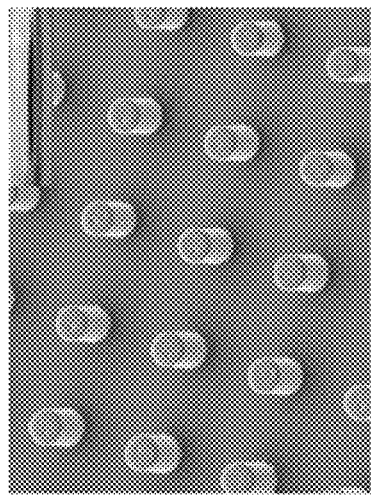
FIG. 12C is an SEM image of PMMA micro pillar arrays (tilted at 20°) for filmwise condensation (S2).

A hot embossing based nanofabrication technique, nanoimprinting lithography (NIL), was used to fabricate polymer micropillars on standard AT-cut 10 MHz QCM substrate. FIG. 12 shows the SEM (JEOL JSM 7401F) images of micropillars for achieving (A) partial wetting condensation (S4), (B) Wenzel condensation (S3), and (C) flood wetting condensation (S2). The insets are the apparent contact angle images for each case.

One of the baselines is related to the full penetration (flooding) state which was achieved by oxygen plasma treating (Harrick PDC-32G Plasma Cleaner) micropillars for 3 minutes followed by the QCM measurement (another baseline is obtained by operating QCM in air). The micropillar surfaces were then dried and modified for different condensation states with the steps described below. For partial wetting condensation surface (S4), micropillars were first coated with a 5 nm gold layer by using a sputter machine (Denton Vacuum Desk IV) and then immersed in a 5 mM 1h, 1h, 2h, 2h-perfluorodecanethiol/ethanol solution for 24 hours to obtain a continuous self-assembled monolayer (SAM) on pillar surface. For Wenzel condensation surface (S3), micropillars were coated with molecular layer of perfluorosilane by molecular vapor deposition (MVD) in a vacuum environment for overnight. Then the Cassie states of two hydrophobic micro pillar surfaces were obtained by loading a macro scale water droplet (Diameter: 8 mm) which covers the whole sensing area. For superhydrophilic surface (S2), micropillar surface was utilized (after plasma treatment) without any further modification. In addition, a smooth gold electrode surface (S1) (contact angle: of 69°) was used as the control.

QCM Based Measurement System

Figures 13A, 13B:
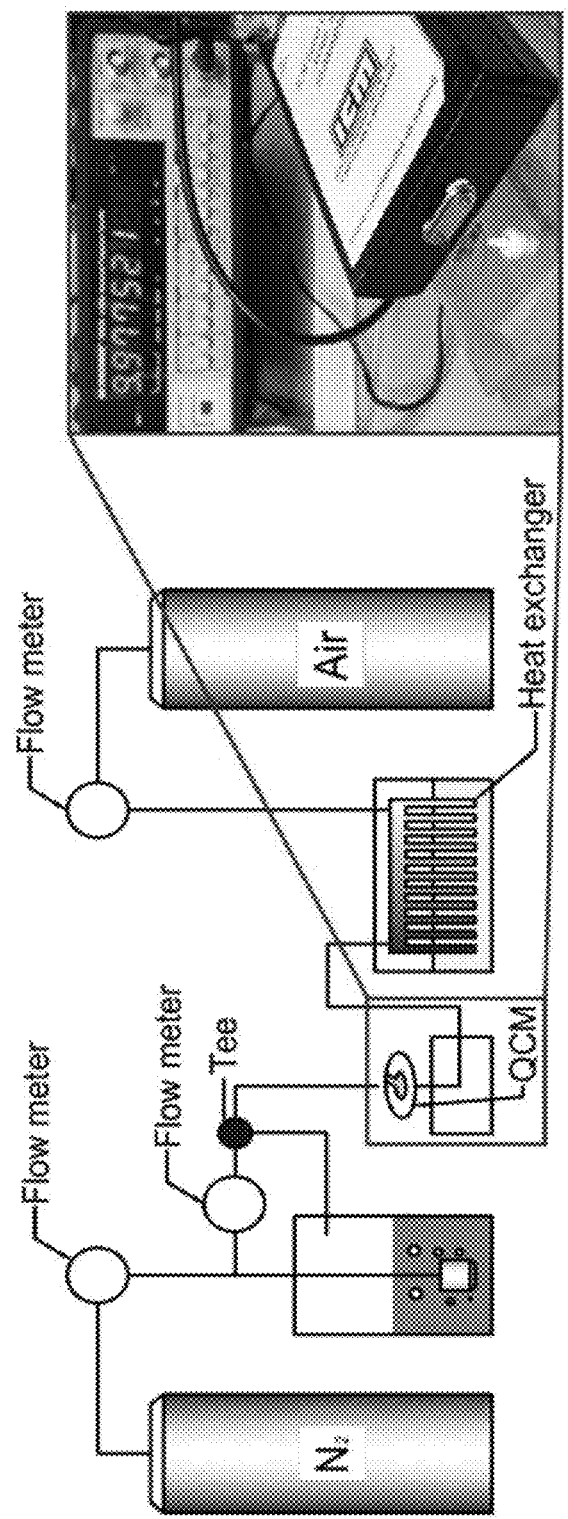
FIG. 13A is a schematic diagram of the QCM based measurement system.
FIG. 13B is a close-up image of part of the QCM based measurement system.
Figure 14C:
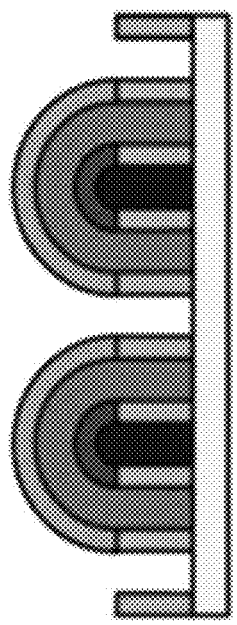
FIG. 14C and FIG. 14D illustrate the growth mode with constant contact angle (CA) mode.
Figure 14D:
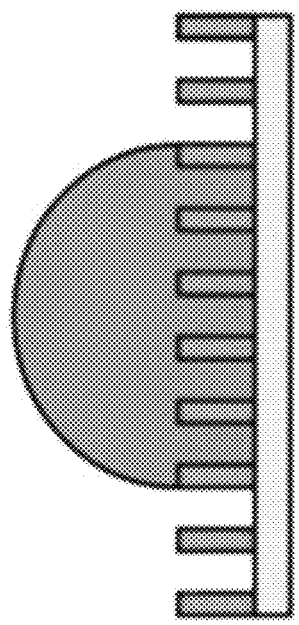
Figure 14A:
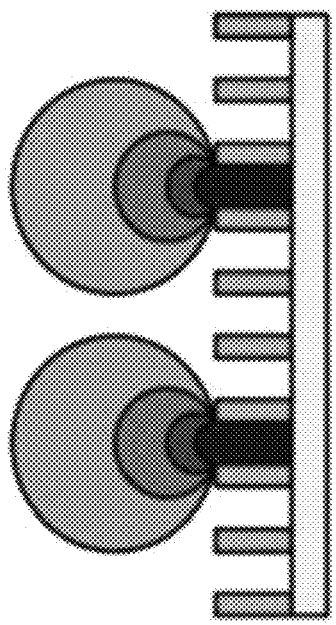
FIG. 14A and FIG. 14B illustrate the two droplet growth mode with constant wetting base (CB) mode.
Figure 14B:
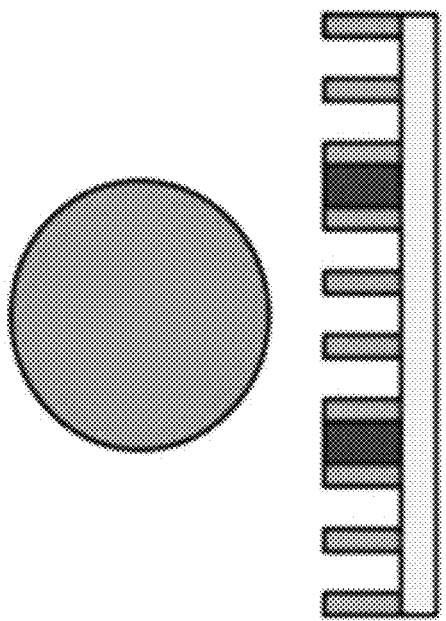

A QCM based condensation measurement system was built. As shown in FIG. 13, the system comprises vapor generation, QCM substrate cooling, and QCM frequency shift measurement subsystems. For vapor generation, dry N$_2$ supplied from a cylinder flow through a bubbler to generate saturated vapor. Two flow meters were used to monitor and control the flow rates of gas N$_2$ and generated vapor. A three-way valve was used to control saturation point by routing the vapor supply either directly to the QCM surface or through a bubbler via an impinger head and then to the QCM surface. To control the temperature of QCM surface, a stream of dry air, supplied from another cylinder firstly flow through a heat exchanger (the coolant of heat exchanger is liquid nitrogen) and then impinge onto the back surface of the QCM (the front surface was constructed with micropillars). During the experiment, the QCM was maintained at 8° C. (calibrated by thermocouples) by keeping the cold airflow of 3 L/min. The QCM with a resonant frequency of 10 MHz was driven by a horizontally oriented lever oscillator (ICM35366-10, Oklahoma) in the experiment. The resonance frequency was monitored and recorded by a frequency counter (BK 1823A, Fotronic Corp.). The frequency data was recorded every 0.25 s and analyzed by a built-in LabView program. In the meantime, images of condensation were captured with an AmScope MU500 camera attached to an Olympus ML-26 microscope and an AMScope trinocular microscope.

Droplet Growth Mechanisms

During the initial stage of condensation, small droplets are grown from the nucleation sites both in between and on top of the micropillars. These tiny droplets continue to grow and coalesce with each other, leading to the formation of Cassie, Wenzel or partial wetting state drops. The drops condensed on the micropillar array could be removable or non-removable depending on two growth modes: constant wetting base (CB) mode or constant contact angle (CA) mode. The droplets nucleating on the top of the micropillars will evolve into drops of Cassie state (removable) and become unconditionally stable while the droplets nucleating on the sidewalls and base of the pillars will grow between pillars and form the wetting spots (FIG. 14). Once the liquid fills in the pillars, it will continue to grow along two possible paths: 1) the liquid grows upward to form droplets with increasing contact angle and size while maintaining the constant wetting base (CB), then the large drop will be generated and removed when small drops coalesces with the neighboring droplet (FIG. 14A); or 2) the liquid between pillars extends horizontally solely beyond the unit cell until coalescing with the neighbor droplets within pillar spaces (FIG. 14B) and the contact angle (CA) is maintained as a constant while wetting base is keep extending during this process[26, 28]. In addition, it is easy to understand that the drops in CB mode have almost spherical shape while the drop growing in CA mode is non-spherical as they are strongly pinned between the pillars.

After the drops in CB mode are removed, the vapor will continue to condense on these wetting spots (FIG. 14A) and grow into next generation of droplets rather than generating some new nucleus which require more energy to overcome the energy barrier. As a result, there are continuous growths of droplets in some fixed wetting areas/spots. However, when the drop grows in CA growth mode, the meniscus of the drop is deformed between micro pillars in order to satisfy the equilibrium contact angle on the sidewalls of micro pillars. The droplets may coalesce and the meniscus of coalesced droplet will keep moving until a new equilibrium is reached. As a result, the drops in CA mode eventually convert into Wenzel state drops.

Four typical condensation scenarios were investigated with proposed QCM technology: a) filmwise condensation on a micropillar surface (S2); b) Wenzel dropwise condensation on a micropillar surface (S3); c) dropwise condensation on a flat hydrophobic surface (S1); and d) partial wetting dropwise condensation on a micropillar surface (S4). Each condensation case was repeated twice for the sake of repeatability. The normalized frequency shift,F, of a QCM device vs. condensation time was reported following an optical microscopic observation.

$$\bar{F} = -\frac{\Delta f - \Delta f_{air}}{\Delta f_{water} - \Delta f_{air}} \quad (11)$$

where $f_{water}$ and $f_{air}$ are the frequency shifts when the surfaces of QCM are submerged in water and air, respectively. These two extreme situations are plotted together with each of the four condensation cases as the controls.

Filmwise Condensation

Figure 15B:
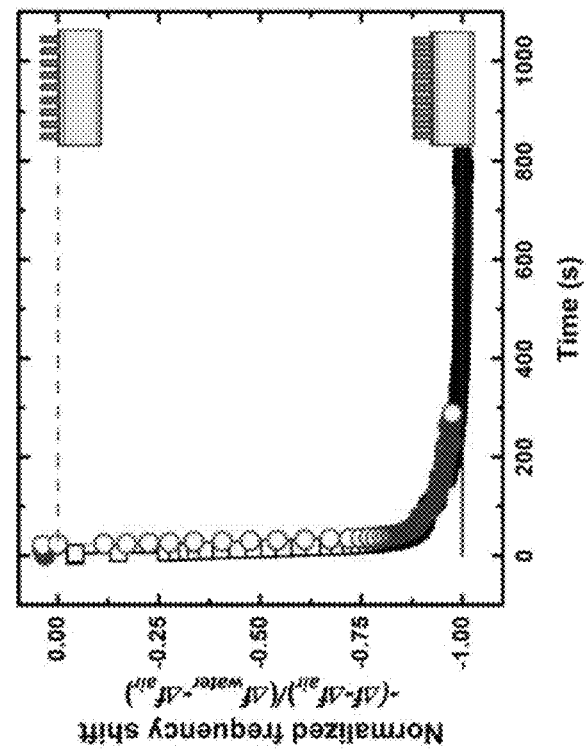
FIG. 15B is a graph of the in situ resonant frequency shift of QCMs for filmwise condensation on superhydrophilic micropillar surfaces (S2).
Figure 15A:
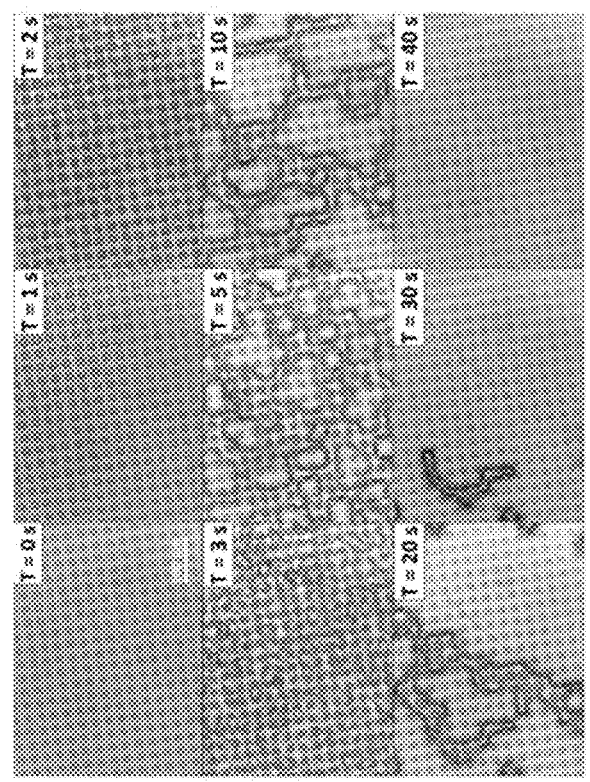
FIG. 15A is a series of optical microscopic images vs. time for filmwise condensation on superhydrophilic micropillar surfaces (S2).

FIG. 15A and FIG. 15B present the optical microscopic observation (FIG. 15A) and corresponding QCM response (FIG. 15B) of vapor condensation on a superhydrophilic micropillar surface (S2). At the beginning (T=0 s to T=1 s), nucleation of droplets takes place on the sidewall of the pillars and the base area of the surface. As the time goes from T=1 s to T=5 s, the droplets grow between pillars and merge into larger drops of irregular shapes. From T=5 s to T=40 s, drops continue to grow and calescence into much larger drops and eventually form a continuous liquid film which covered the micropillars surface in microscopic image region. Several regions covered with liquid films merge together and eventually cover the whole pillar surface from T=40 s to T=300 s. In terms of QCM measurement (FIG. 15B), the normalized frequency shift (Eq. (C2)) of QCM is near the dry baseline before the occurrence of condensation. With the progress of nucleation and droplet growth, the resonant frequency sharply drops and eventually level off until a full coverage of the water film over the pillar surface is formed.

Wenzel Dropwise Condensation

Figure 16B:
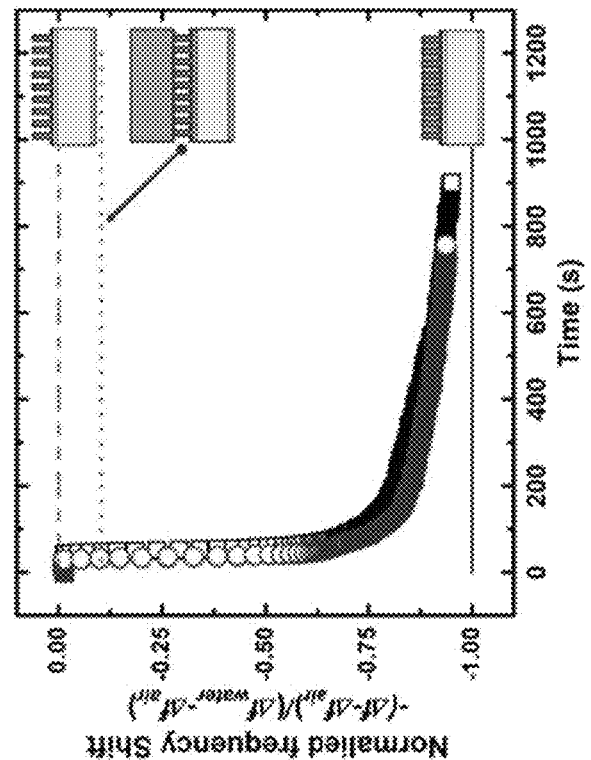
FIG. 16B is a graph of the in situ resonant frequency shift of QCMs for Wenzel state condensation dropwise condensation on a hydrophobic micropillar surface (S3) with perfluorosilane MVD coating.
Figure 16A:
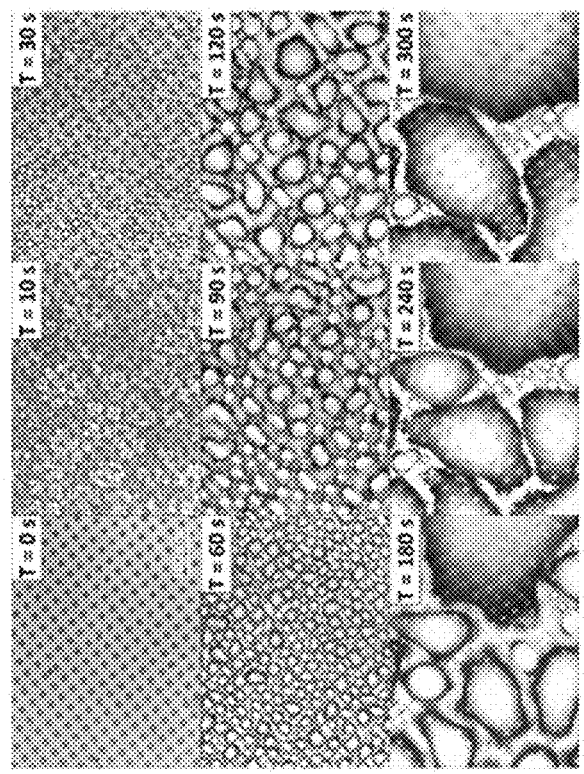
FIG. 16A is a series of optical microscopic images vs. time for Wenzel state condensation dropwise condensation on a hydrophobic micropillar surface (S3) with perfluorosilane MVD coating.

FIG. 16A shows the time-lapse top-view images of Wenzel dropwise condensation on the micropillar surface. Different from filmwise condensation, most of the droplets were nucleated between pillars within 30 s (T=0 s to T=30s), followed by the coalescence of the droplets into larger drops which stay pinned in the space between adjacent pillars from T=30 s to T=60 s. The meniscuses of the drops become curved and then irregular—a typical phenomenon of CA growth. The non-spherical drops kept growing and coalescence into larger drops (T=90 s to T=300 s), until the whole surface was almost fully covered by a few big Wenzel state drops.

For the QCM frequency response (FIG. 16B), after the dropping stage due to nucleation, the resonant frequency gradually approaches the complete wetting stage instead of decreasing in a quick manner like filmwise condensation (superhydrophilic pillar surface). It is believed that the pillar surfaces keep the liquid pinned between pillars from receding freely; the growth of drops can only be achieved through coalescence, which is a slow process. As a result, the spaces in between the micro pillars were filled by condensed water gradually and frequency shift decrease slowly. However, once the spared space between pillars is filled, the hydrophobicity of such pillar surface is continuously reduced until completely lost (T>1000 s). It is worth noting that the nucleation on hydrophilic surface is usually faster than hydrophobic surface as a lower free energy barrier is required for this process.

Dropwise Condensation on Flat Surface

Figures 17A, 17B:
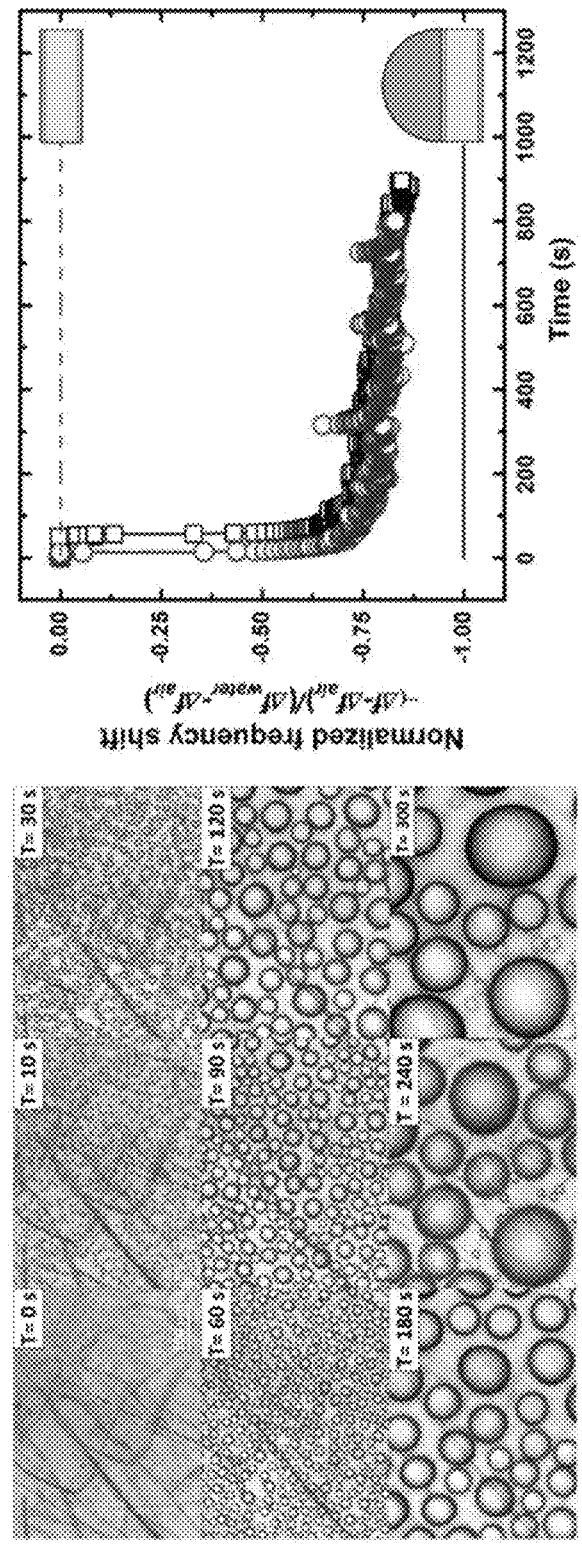
FIG. 17A is a series of optical microscopic images vs. time for typical dropwise condensation on a flat hydrophobic surface (contact angle 67°) (S1).
FIG. 17B is a graph of the in situ resonant frequency signals of QCMs for typical dropwise condensation on a flat hydrophobic surface (contact angle 67°) (S1).
Figure 18:
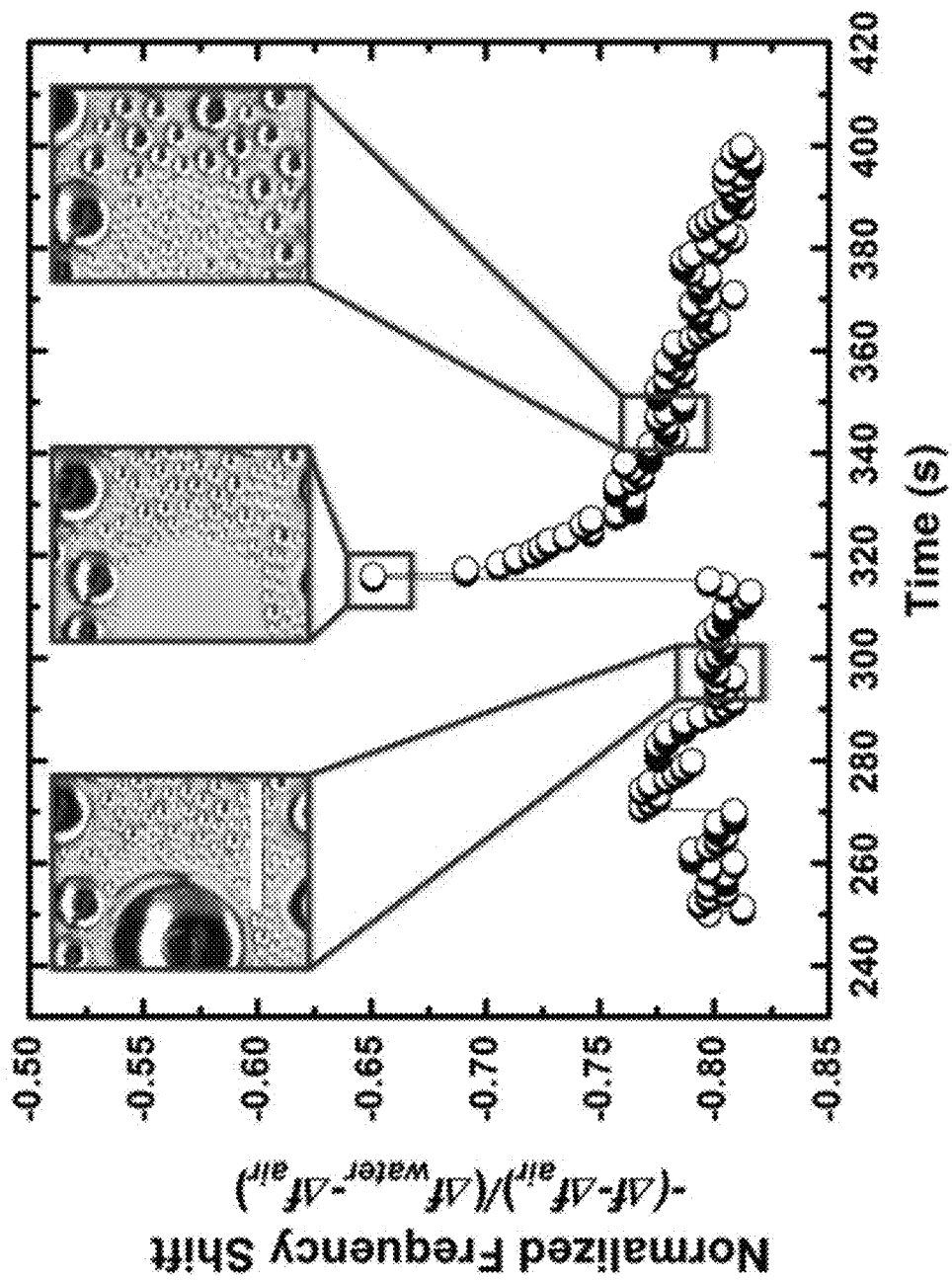
FIG. 18 is a graph of QCM frequency signals and correlated microscopic images about surface mass fluctuation. The scale bar of the inset images is 1 mm.

FIG. 17A and FIG. 17B illustrate the microscopic images and the QCM signal of typical dropwise condensation on a flat hydrophobic surface. The beginning (T=0 s to T=10s), is the same as the previous case that nucleation and initial droplets growth and the resonant frequency drop sharply. However, after 100 s (T=90 s to T=300 s), fluctuations of frequency shift appear. This is because the coalesced water droplets recede from originally occupied surface areas in order to maintain a fixed contact angle (CA mode) since there is no pinning caused by pillar structure. This results in the sudden change of surface coverage and reduction of frequency shift. After this, the new droplets will nucleate on the left open/re-exposed surfaces, which increase the frequency shift again. The images and corresponding QCM frequency signal are shown in FIG. 18.

In summary, this resonant frequency fluctuation was induced due to the competition between droplet receding and re-nucleation.

Partial Wetting Dropwise Condensation

Figure 19B:
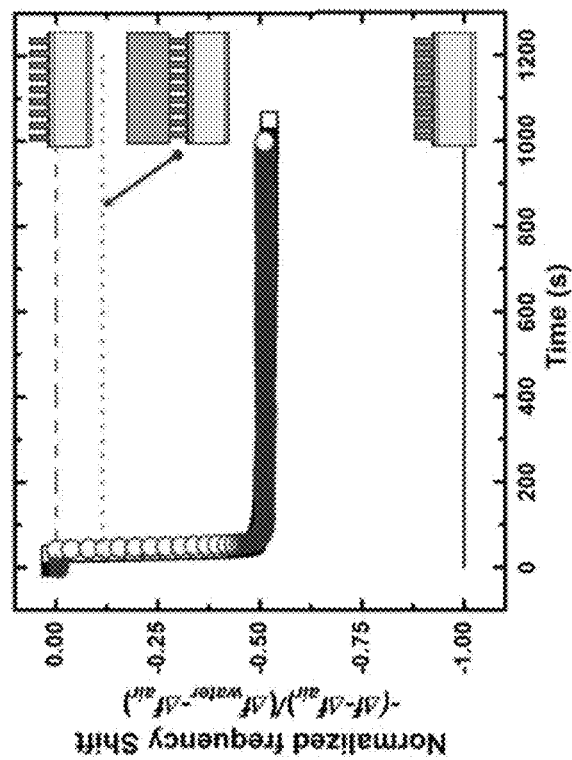
FIG. 19B is a graph of in situ QCM resonant frequency signals for partial wetting dropwise condensation on a hydrophobic micropillar (d/l=0.7) surface with perfluorodecanethiol SAM coating (S4).
Figure 19A:
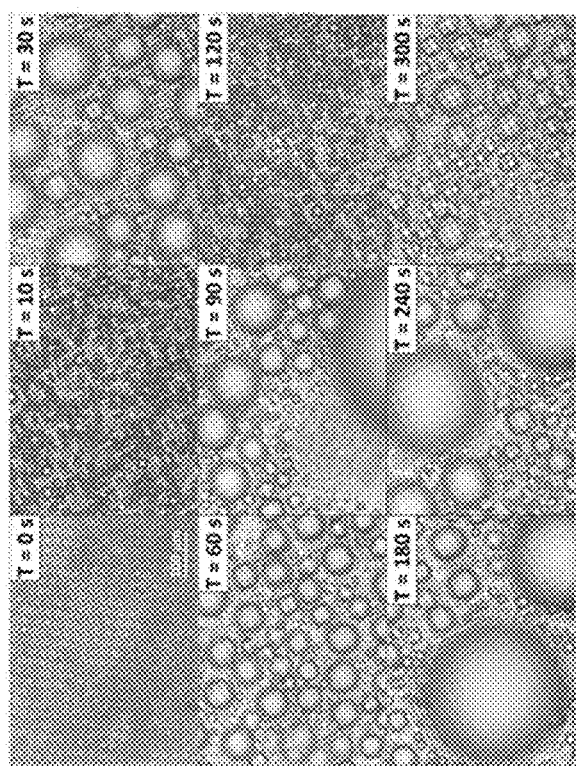
FIG. 19A is a series of optical microscopic images vs. time for partial wetting dropwise condensation on a hydrophobic micropillar (d/l=0.7) surface with perfluorodecanethiol SAM coating (S4).

The images of partial wetting condensation and QCM response are depicted in FIG. 19A and FIG. 19B. It can be observed that all the droplets in this condensation are spherical shape and easily removed because these drops were not pinned in micro pillars array. Comparing the drop growth shown in FIG. 19A (partial wetting drop-wise condensation) with that of FIG. 16A (Wenzel condensation) at T=30 s, more and bigger droplets have been formed and quickly removed on the partially wetting surface (S4) while very a few smaller droplets were formed and grow slowly into bigger drops on Wenzel condensation surface (S3). It is apparent that the partial wetting drop-wise condensation on hydrophobic surface has much higher efficiency than Wenzel drop-wise condensation does. At T=90s, separated wetting spots can be seen after the bigger drops removal. From T=120 s to T=300s, a new generation of droplets experience nucleation, growing, coalescence and removal in CB growth mode (FIG. 14A) and this process repeats itself continuously. For the resonant frequency of QCM device, it become quickly stable at a level far above the level caused by flooding wetting, which is believed, caused by wetting spots between pillar spaces. During the whole condensation, these spots won't increase their number and size (61.7% of pillar space would be wetting spots) and drops grow in CB growth mode.

Wetting State Transition

Figure 20A:
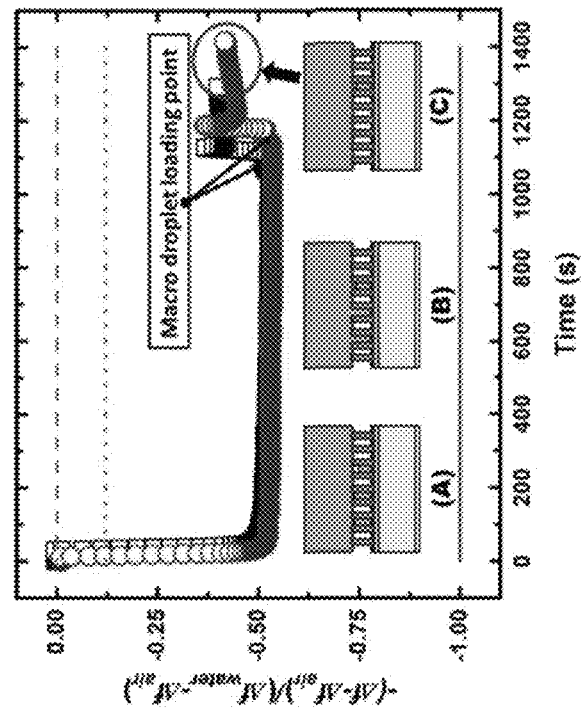
FIG. 20A is a graph vs. time for wetting state transitions between Cassie and Wenzel on a flat surface.

Another important phenomenon in dropwise condensation on hydrophobic surfaces is the transition between Wenzel and Cassie state. In this experiment, a macro scale drop (8 mm) was loaded on a hydrophobic flat surface and a partial wetting hydrophobic pillar surface after dropwise condensation. For the flat hydrophobic surface, the resonant frequency shift shows that the dropwise condensation quickly become complete wetting without any transition between Wenzel state and Cassie state shown in FIG. 20A.

Figure 20B:
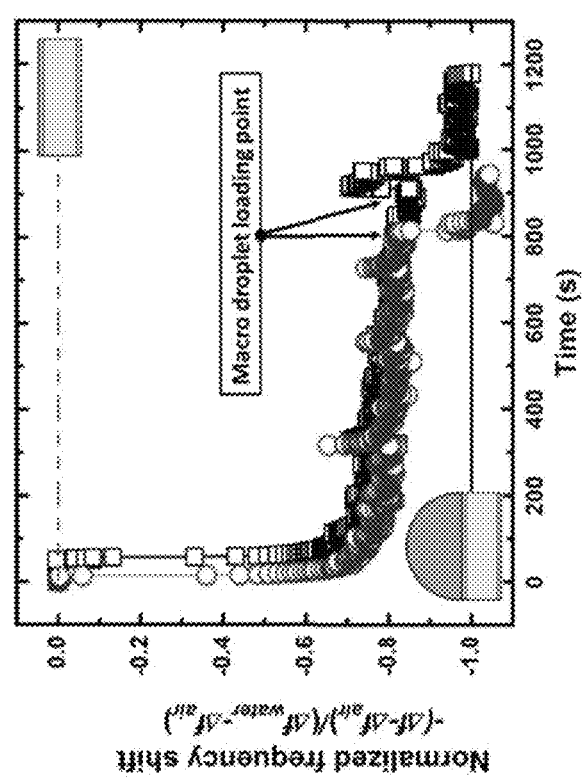
FIG. 20B is a graph vs. time for wetting state transitions between Cassie and Wenzel on a partial wetting hydrophobic micropillar surface.
Figure 21:
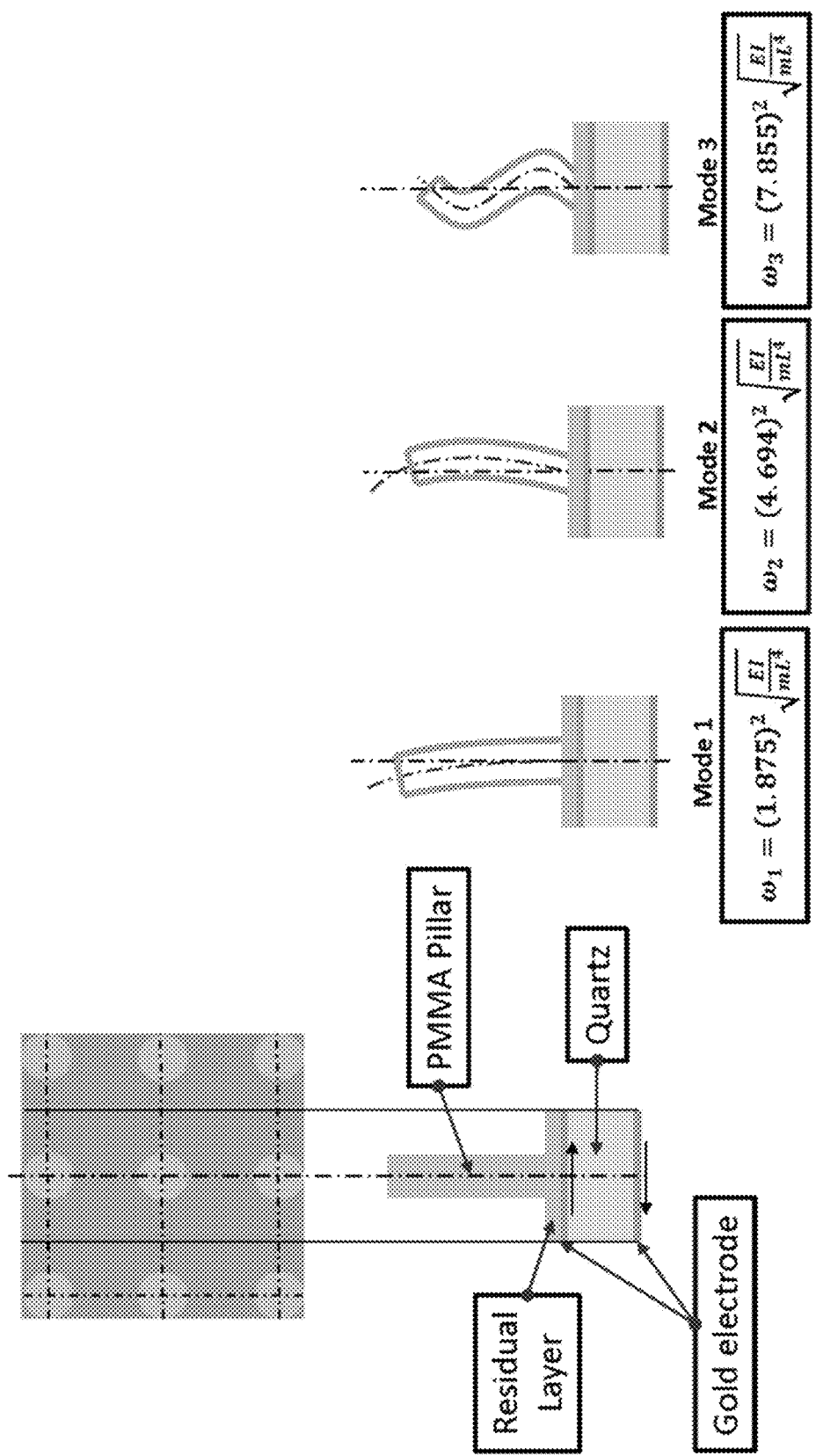
FIG. 21 is a schematic diagram illustrating different vibration modes for a QCM-P device.
Figure 22A:
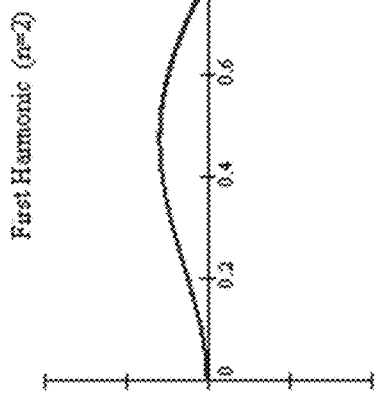
FIG. 22A is a graph illustrating a fundamental vibration mode of a QCM-P device as a function of distance along a pillar.
Figure 22B:
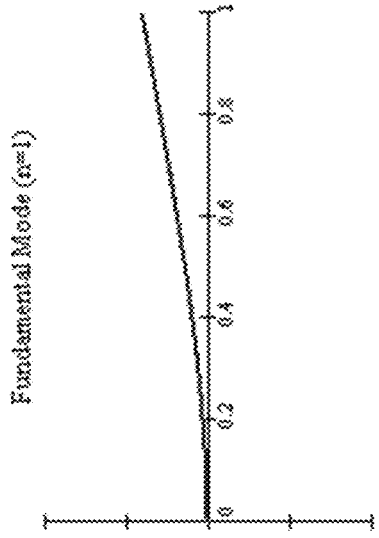
FIG. 22B is a graph illustrating a first harmonic vibration mode of a QCM-P device as a function of distance along a pillar.
Figure 22C:
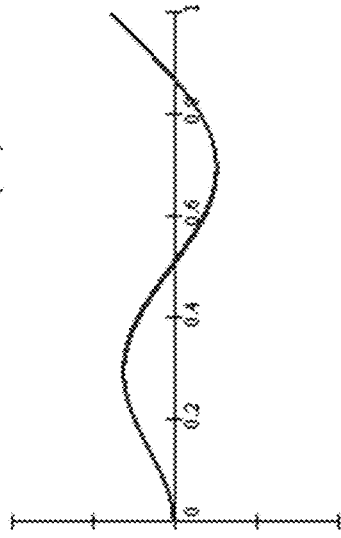
FIG. 22C is a graph illustrating a second harmonic vibration mode of a QCM-P device as a function of distance along a pillar.
Figure 23:
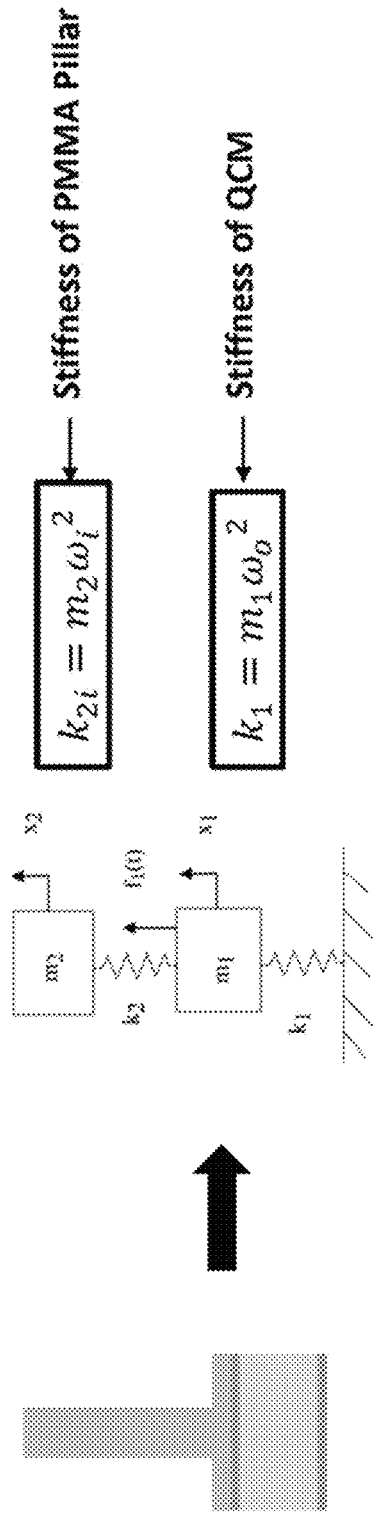
FIG. 23 is an illustration of a derivation of an impedance matrix for a QCM-P device.
Figure 24:
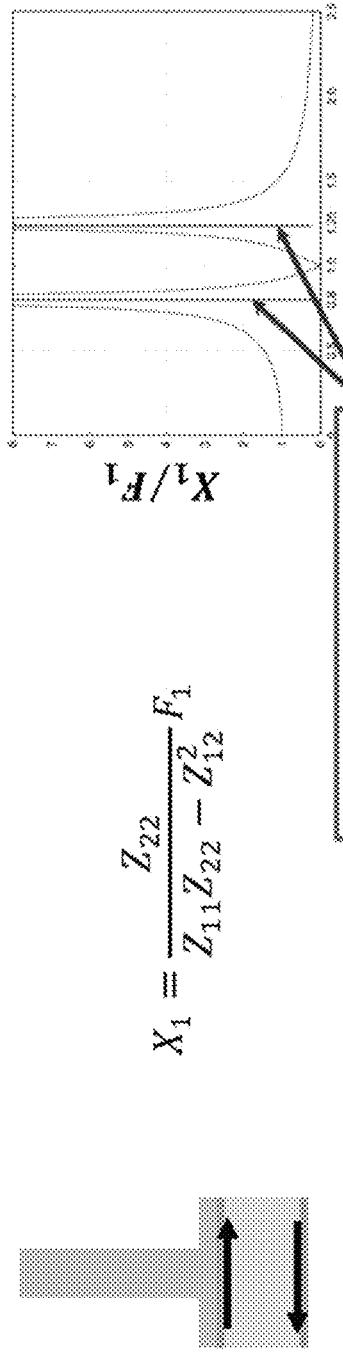
FIG. 24 is an illustration of a derivation of the result that a QCM-P device embodying principles of the invention will have at least two resonant frequencies.
Figure 25:
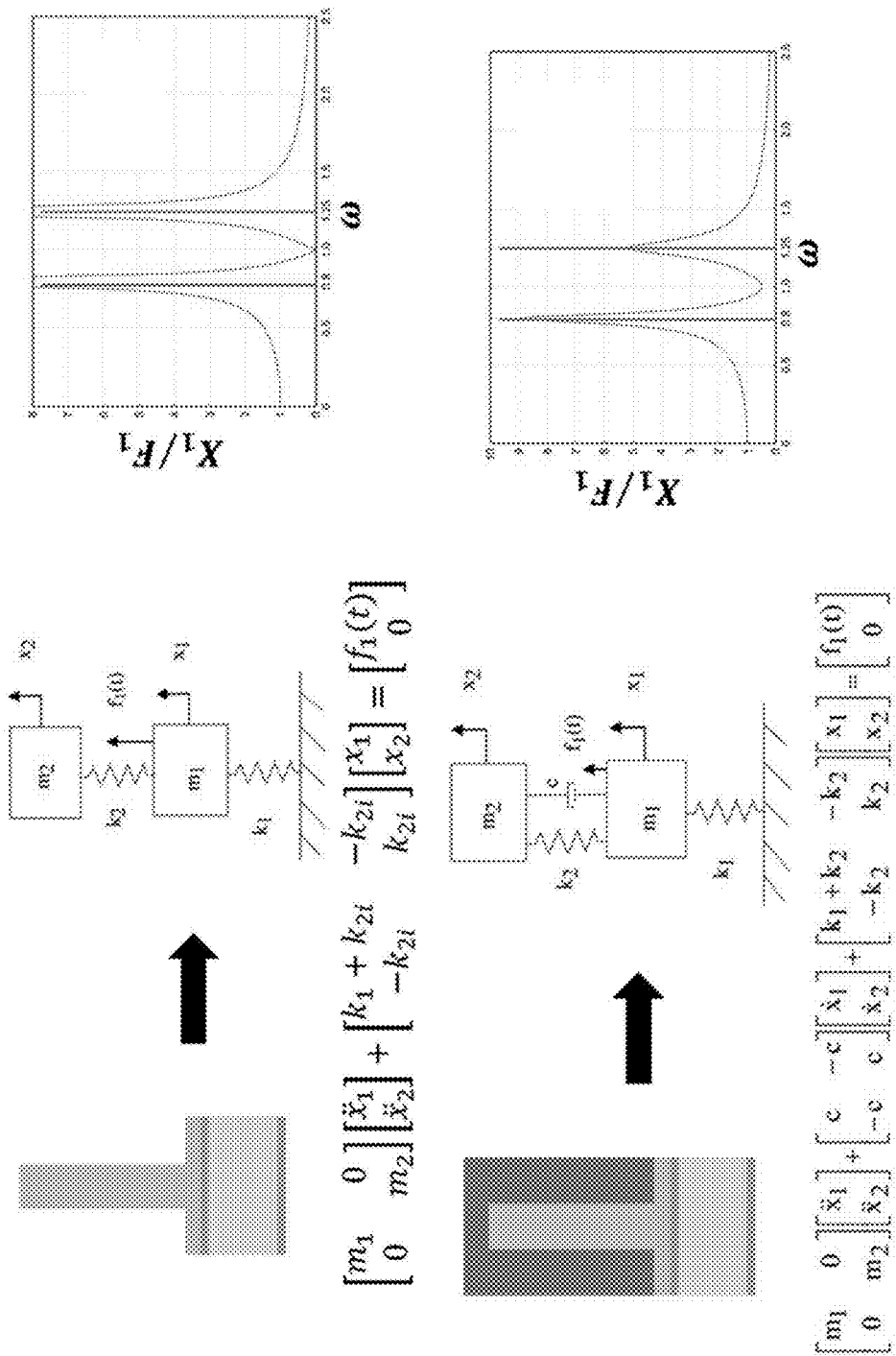
FIG. 25 is an illustration of a derivation showing that a more dense medium surrounding a QCM-P device embodying principles of the invention will reduce a resonant frequency of the device.
Figure 26:
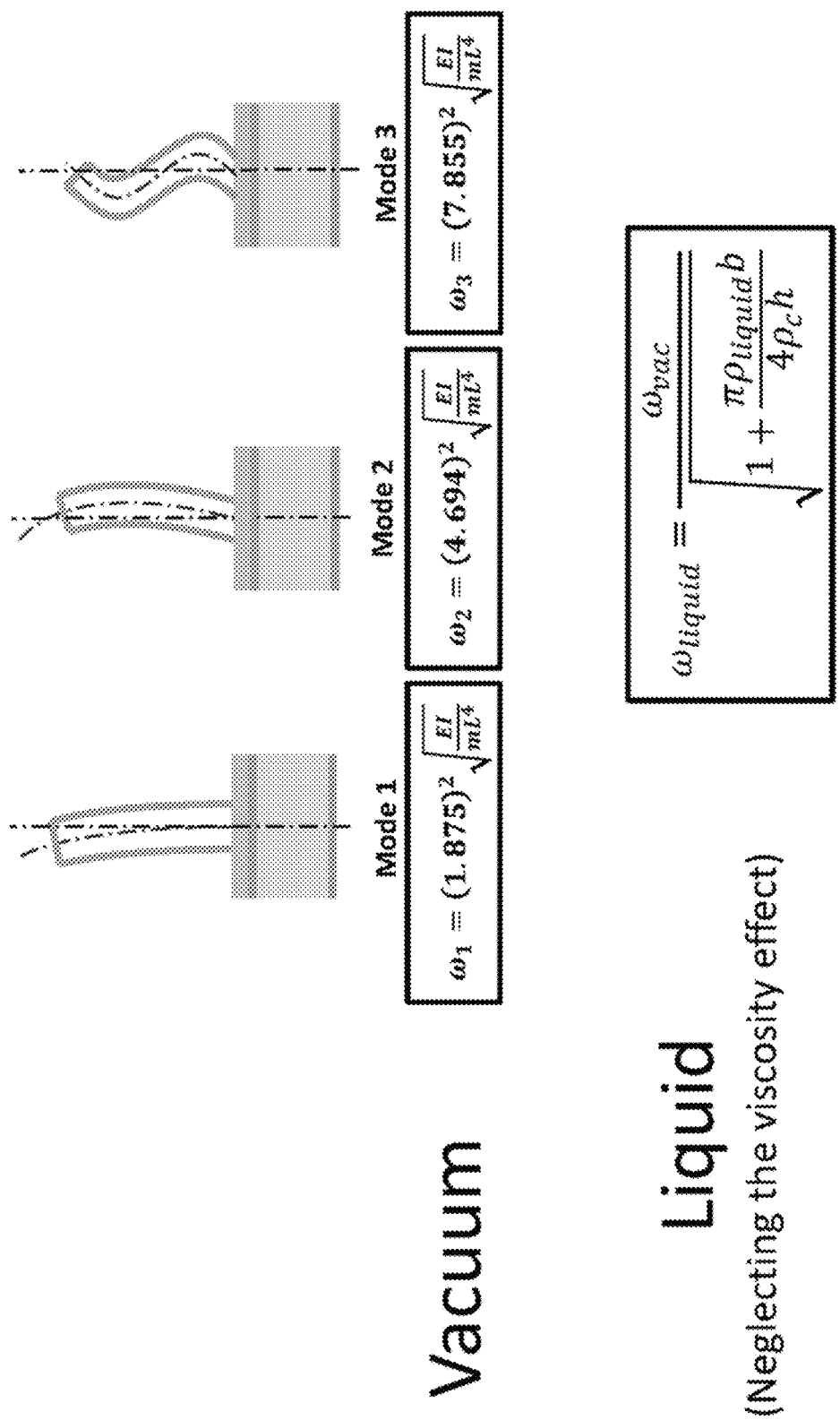
FIG. 26 is an illustration showing the closed form solution for a QCM-P device embodying principles of the invention surrounded by a more dense medium.
Figure 27A:
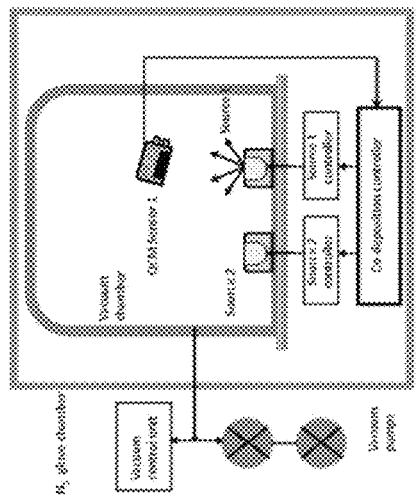
FIG. 27A is graph of normalized resonant frequency vs. pillar height.
Figure 27B:
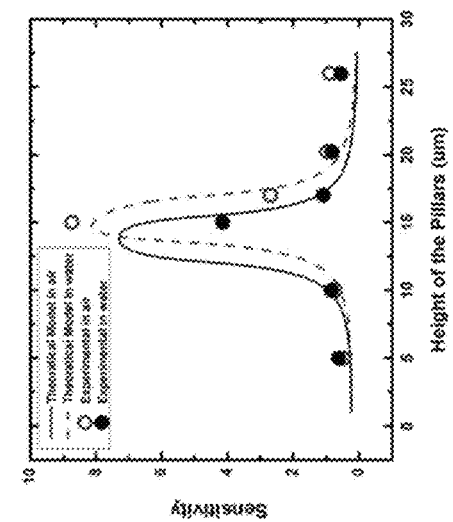
FIG. 27B is a schematic diagram of a system used to fabricate QCM-P devices embodying principles of the invention.
Figure 27C:
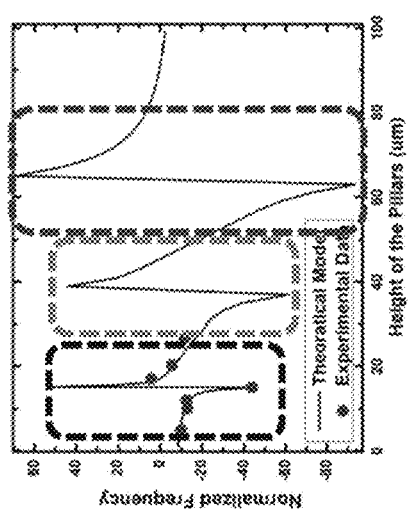
FIG. 27C is a more detailed graph of normalized resonant frequency vs. pillar height.
Figure 27D:
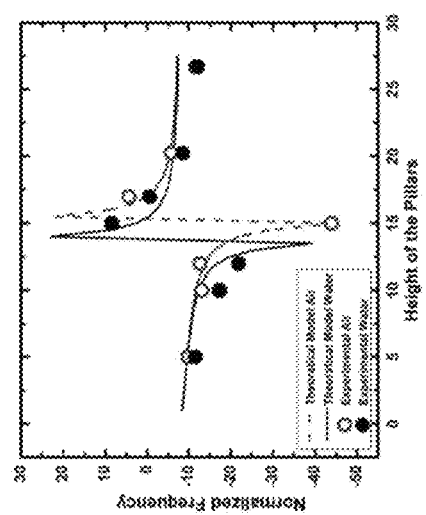
FIG. 27D is a graph of sensitivity vs. pillar height.
Figures 28A, 28B:
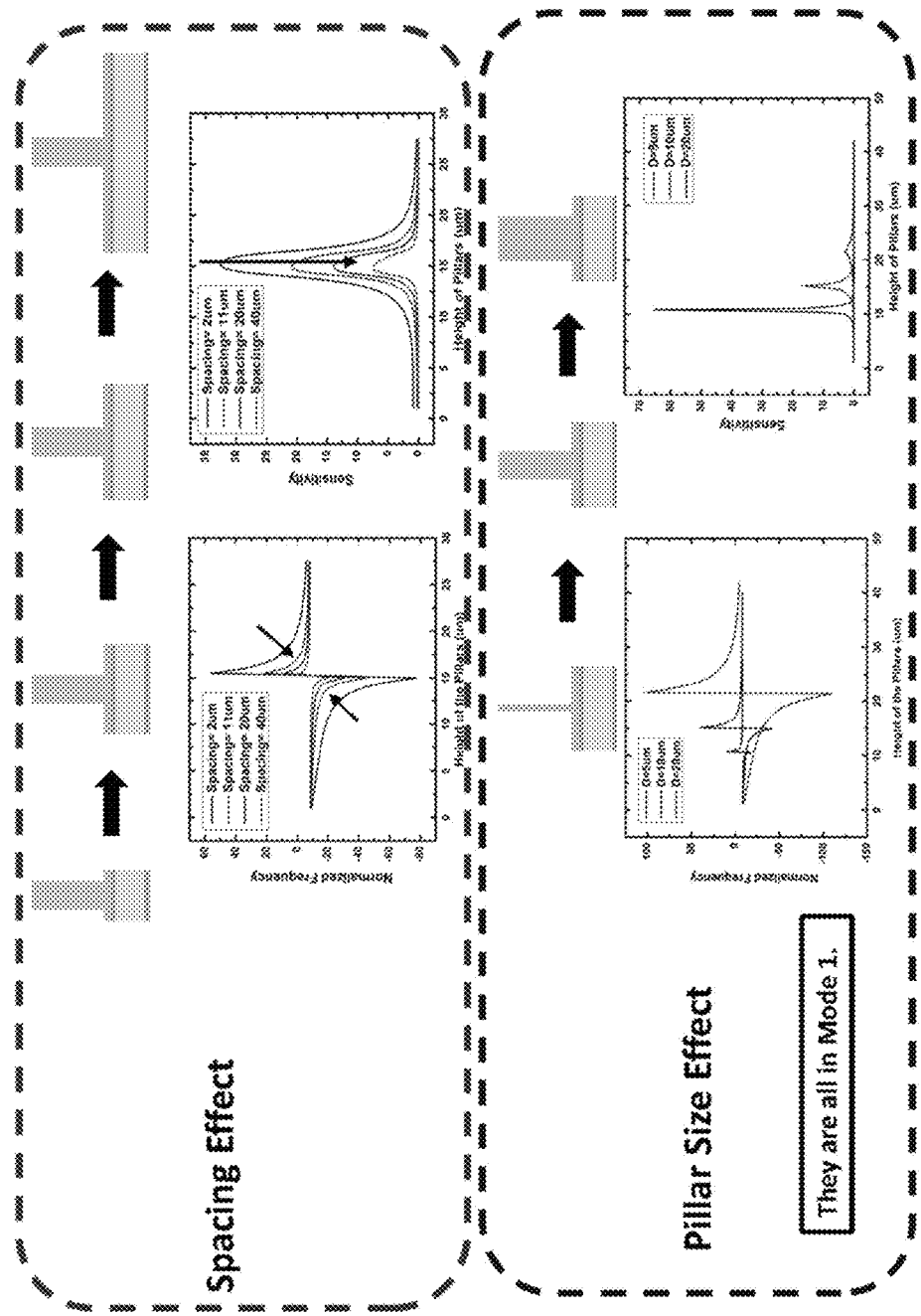
FIG. 28A is a diagram showing the effect of spacing between pillars. The sensitivity decreases and the normalized frequency sharpens as the spacing is increased.
FIG. 28B is a diagram showing the effect of pillar size (e.g., diameter for cylindrical pillars). The sensitivity decreases and the normalized frequency sharpens as the size is increased.
Figure 31B:
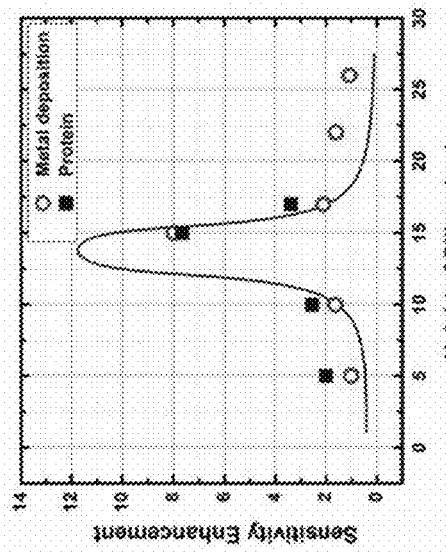
FIG. 31B is graph of sensitivity enhancement vs pillar height for measurement with QCM-P devices using both metals and biological materials as samples of interest.
Figure 31A:
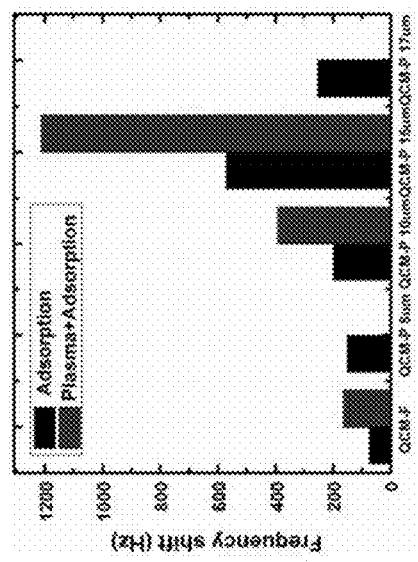
FIG. 31A is a bar graph showing data for measurements using various QCM-P devices.
Figure 31C:
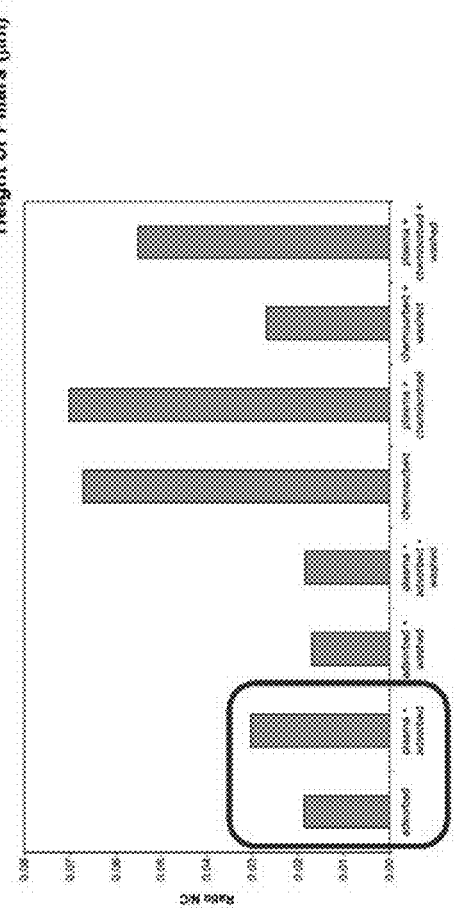
FIG. 31C is a bar graph showing data for materials adsorbed on QCM-P devices by different methods.

However, for partial wetting hydrophobic micro-pillar surface, a transition from Wenzel-to-Cassie would be highly possible and has been observed. This phenomenon is first quantitatively measured using QCM technique in this work (FIG. 20B). As the Cassie state is energetically favored compared to Wenzel state, the wetting spots are at a metastable state. When the macro scale drop (8 mm) was loaded on the pillar surface (height: 22 um, spacing: 10 um, diameter: 7 um), some of the elongated wetting spots lying underneath the Cassie drop transit from Wenzel to Cassie immediately as soon as they were in contact with the Cassie drop causing an increase of frequency shift of the QCM (FIG. 20B). Around 23.5% of wetting spots were transited from Wenzel state to Cassie state based on the QCM frequency shift data, which not only proves the existence of the transition from Wenzel state to Cassie state, a favorable transition state for some elongated wetting spots, but also provides a method to quantitatively study the dynamic transition speed and the amount of transition.

We have presented a unique method to quantitatively analyze different vapor condensation behaviors on different micropillar based surfaces. Nanoimprint Lithography (NIL) was used to fabricate these micro pillars on QCM substrates. For the filmwise condensation on a superhydrophilic pillar surface, the resonant frequency of QCM quickly dropped down to the complete wetting level due to a quick growth of water film. Three typical drop-wise condensations (flat hydrophobic, Wenzel condensation, partial wetting condensation) on hydrophobic surfaces were studied with a combined optical imaging and QCM dynamic signal analysis approach. For the condensation on a flat hydrophobic surface, the frequency shift of QCM oscillates due to the change of wetting surface caused by drop receding and re-growth. For the Wenzel condensation surface, the QCM resonant frequency gradually decreases to the complete flooding level due to the loss of hydrophobicity resulted by CA growth mode and pinning effect. The partial wetting condensation shows a stable QCM frequency shift signal, which corresponds to a 61.7% of wetting surface. These separated wetting spots remain unchanged during continuous drop-wise condensation process or in a constant base mode. The transition from Wenzel state to Cassie state was first quantitatively probed by loading a macro scale drop on hydrophobic micro-pillar surface (after partial wetting condensation), which manifests the capacity of QCM based system for analyzing dynamics of wettability and condensation process.

Definitions

Any reference in the claims to an electronic signal or an electromagnetic signal (or their equivalents) is to be understood that in a preferred embodiment the signal is a non-transitory electronic signal or a non-transitory electromagnetic signal. If the signal per se is not claimed, the reference may in some instances be to a description of a propagating or transitory electronic signal or electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Incorporation by Reference

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A quartz crystal microbalance resonator, comprising:
a quartz oscillator having a surface and having electrical input terminals, and
a plurality of micropillars of a resonant material, each of the micropillars having a diameter, a height, and a spacing, together forming a patterned array of micropillars, and
a residual layer situated between said plurality of micropillars and said quartz oscillator,
wherein
said resonant material is a polymer,
said plurality of micropillars in mechanical communication with said surface of said quartz oscillator, and
said quartz microbalance resonator having at least one characteristic resonant frequency,
wherein said quartz crystal microbalance resonator is configured to modify said at least one characteristic resonant frequency in response to a quantity of adsorbed material on said plurality of micropillars.

2. The quartz crystal microbalance resonator of claim 1, wherein said at least one characteristic resonant frequency has a dependence on said diameter, said height and said spacing of said micropillars.

3. The quartz crystal microbalance resonator of claim 1, wherein said quartz crystal microbalance resonator is configured to operate in contact with a fluid medium.

4. The quartz crystal microbalance resonator of claim 3, wherein said fluid medium is a gas.

5. The quartz crystal microbalance resonator of claim 3, wherein said fluid medium is a liquid.

6. The quartz crystal microbalance resonator of claim 1, wherein said resonant material is polymethyl methacrylate.

7. The quartz crystal microbalance resonator of claim 1, wherein each of said micropillars is a cylindrical pillar.

8. The quartz crystal microbalance resonator of claim 7, wherein said cylindrical pillar has a height in the range of 5 µm to 25 µm.

9. The quartz crystal microbalance resonator of claim 8, wherein said cylindrical pillar has a height in the range of 10 µm to 20 µm.

10. A method of operating a quartz crystal microbalance resonator, comprising the steps of:
providing a quartz crystal microbalance resonator of claim 1;
operating said quartz crystal microbalance resonator to determine one of said at least one characteristic resonant frequency;
adsorbing a quantity of a substance on said plurality of pillars;
operating said quartz crystal microbalance resonator to determine a frequency shift in said one of said at least one characteristic resonant frequency;
calculating a value of a mass of said quantity of said substance that was adsorbed on said plurality of pillars from said frequency shift; and
performing at least one of recording said value, transmitting said value to a data handling system, or to displaying said value to a user.

11. The method of operating a quartz crystal microbalance resonator of claim 10, wherein said at least one characteristic resonant frequency is a fundamental frequency.

12. The method of operating a quartz crystal microbalance resonator of claim 10, wherein said at least one characteristic resonant frequency is a first harmonic frequency.

13. The method of operating a quartz crystal microbalance resonator of claim 10, wherein said at least one characteristic resonant frequency is a second harmonic frequency.

* * * * *